US012665511B2

(12) United States Patent (10) Patent No.: US 12,665,511 B2
Kalfas et al. (45) Date of Patent: \*Jun. 23, 2026

(54) SYSTEM AND METHOD FOR ACTIVATING AN ANALYTE MONITORING SYSTEM

(71) Applicant: Dexcom, Inc., San Diego, CA (US)

(72) Inventors: Nicholas Kalfas, San Diego, CA (US); Gary Thomas Neel, Dania Beach, FL (US)

(73) Assignee: Dexcom, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/795,831

(22) Filed: Aug. 6, 2024

(65) Prior Publication Data

US 2024/0396453 A1 Nov. 28, 2024

Related U.S. Application Data

(63) Continuation of application No. 18/159,659, filed on Jan. 25, 2023, now Pat. No. 12,088,201.

(Continued)

(51) Int. Cl.
*H02M 3/158* (2006.01)
*A61B 5/00* (2006.01)
(Continued)

(52) U.S. Cl.
CPC ........... *H02M 3/158* (2013.01); *A61B 5/6833* (2013.01); *G01R 19/16576* (2013.01);
(Continued)

(58) Field of Classification Search
CPC .. H02M 3/158; A61B 5/6833; A61B 5/14546; A61B 2560/0209;
(Continued)

(56) References Cited

U.S. PATENT DOCUMENTS 9,898,120 B2 * 2/2018 Rhee ....................... G06F 21/31
2006/0229520 A1 * 10/2006 Yamashita ............. A61B 5/681
600/503

(Continued)

FOREIGN PATENT DOCUMENTS

EP 3841967 A1 6/2021

OTHER PUBLICATIONS

International Search Report and Written Opinion for Application No. PCT/US2023/061313 mailed Apr. 19, 2023, 13 pages.

*Primary Examiner* — Rexford N Barnie
*Assistant Examiner* — Terrence R Willoughby
(74) *Attorney, Agent, or Firm* — Klarquist Sparkman, LLP

(57) ABSTRACT

Aspects of the present disclosure provide a power activation module for powering one or more wearable electronic components. The power activation module includes a switch configured to provide a path for current flow between a battery associated with the power activation module, the one or more wearable electronic components, and a ground terminal. The power activation module also includes a sensor configured to detect whether a signal is applied to the sensor and, based on the detection, output a first digital output signal for controlling, at least in part, the switch to control the current flow from the battery to the one or more wearable electronic components. The power activation module also includes a lock pin configured to receive a lock signal, wherein when the lock signal is received, the switch is locked to allow current flow from the battery to the one or more wearable electronic components.

20 Claims, 9 Drawing Sheets

Related U.S. Application Data

(60) Provisional application No. 63/267,228, filed on Jan. 27, 2022.

(51) Int. Cl.

| | |
|---|---|
| *A61B 5/145* | (2006.01) |
| *G01R 19/165* | (2006.01) |
| *G01R 33/09* | (2006.01) |

(52) U.S. Cl.
CPC ........ *G01R 33/098* (2013.01); *A61B 5/14546* (2013.01); *A61B 2560/0209* (2013.01)

(58) Field of Classification Search
CPC ........ A61B 2560/0214; A61B 5/14532; G01R 19/16576; G01R 33/098; H02J 7/0032; H02J 9/005

See application file for complete search history.

(56) References Cited

U.S. PATENT DOCUMENTS

| | | |
|---|---|---|
| 2018/0026678 A1 | 1/2018 | Biederman |
| 2018/0360326 A1 | 12/2018 | Lee et al. |
| 2018/0368961 A1 * | 12/2018 | Shanjani .............. A61B 5/4547 |
| 2019/0246977 A1 | 8/2019 | Miller et al. |
| 2019/0342637 A1 | 11/2019 | Halac et al. |

* cited by examiner

SYSTEM AND METHOD FOR ACTIVATING AN ANALYTE MONITORING SYSTEM

CROSS-REFERENCE TO RELATED APPLICATIONS

This application is a continuation of U.S. patent application Ser. No. 18/159,659, filed Jan. 25, 2023, which claims benefit of and priority to U.S. Provisional Application No. 63/267,228, filed Jan. 27, 2022. Each of the aforementioned applications is incorporated by reference herein in its entirety, and each is hereby expressly made a part of this specification.

TECHNICAL FIELD

The present disclosure relates generally to an electronic device, such as a wearable device for monitoring analyte values received from a sensor. More particularly, the present disclosure is directed to power activation techniques for the electronic device.

BACKGROUND

Diabetes is a metabolic condition relating to the production or use of insulin by the body. Insulin is a hormone that allows the body to use glucose for energy, or store glucose as fat. When a person cats a meal that contains carbohydrates, the food is processed by the digestive system, which produces glucose in the person's blood. Blood glucose can be used for energy or stored as fat. The body normally maintains blood glucose levels in a range that provides sufficient energy to support bodily functions and avoids problems that can arise when glucose levels are too high, or too low. Regulation of blood glucose levels depends on the production and use of insulin, which regulates the movement of blood glucose into cells.

When the body does not produce enough insulin, or when the body is unable to effectively use insulin that is present, blood sugar levels can elevate beyond normal ranges. The state of having a higher-than-normal blood sugar level is called "hyperglycemia." Chronic hyperglycemia can lead to several of health problems, such as cardiovascular disease, cataract and other eye problems, nerve damage (neuropathy), and kidney damage. Hyperglycemia can also lead to acute problems, such as diabetic ketoacidosis—a state in which the body becomes excessively acidic due to the presence of blood glucose and ketones, which are produced when the body cannot use glucose. The state of having lower than normal blood glucose levels is called "hypoglycemia." Severe hypoglycemia can lead to acute crises that can result in seizures or death.

A diabetes patient can receive insulin to manage blood glucose levels. Insulin can be received, for example, through a manual injection with a needle. Wearable insulin pumps are also available. Diet and exercise also affect blood glucose levels.

Diabetes conditions are sometimes referred to as "Type 1" and "Type 2". A Type 1 diabetes patient is typically able to use insulin when it is present, but the body is unable to produce adequate insulin, because of a problem with the insulin-producing beta cells of the pancreas. A Type 2 diabetes patient may produce some insulin, but the patient has become "insulin resistant" due to a reduced sensitivity to insulin. The result is that even though insulin is present in the body, the insulin is not sufficiently used by the patient's body to effectively regulate blood sugar levels.

SUMMARY

Aspects of the present disclosure a provide power activation module for powering one or more wearable electronic components. In some embodiments, the power activation module includes a switch configured to provide a path for current flow between a battery associated with the power activation module, the one or more wearable electronic components, and a ground terminal. Additionally, in some embodiments, the power activation module includes a sensor configured to detect whether a signal is applied to the sensor and, based on the detection, output a first digital output signal for controlling, at least in part, the switch to control the current flow from the battery to the one or more wearable electronic components. Additionally, in some embodiments, the power activation module includes a lock pin configured to receive a lock signal, wherein when the lock signal is received, the switch is locked to allow current flow from the battery to the one or more wearable electronic components.

BRIEF DESCRIPTION OF THE DRAWINGS

Further aspects of the present disclosure will be more readily appreciated upon review of the detailed description of the various disclosed embodiments, described below, when taken in conjunction with the accompanying figures.

Figure 1:
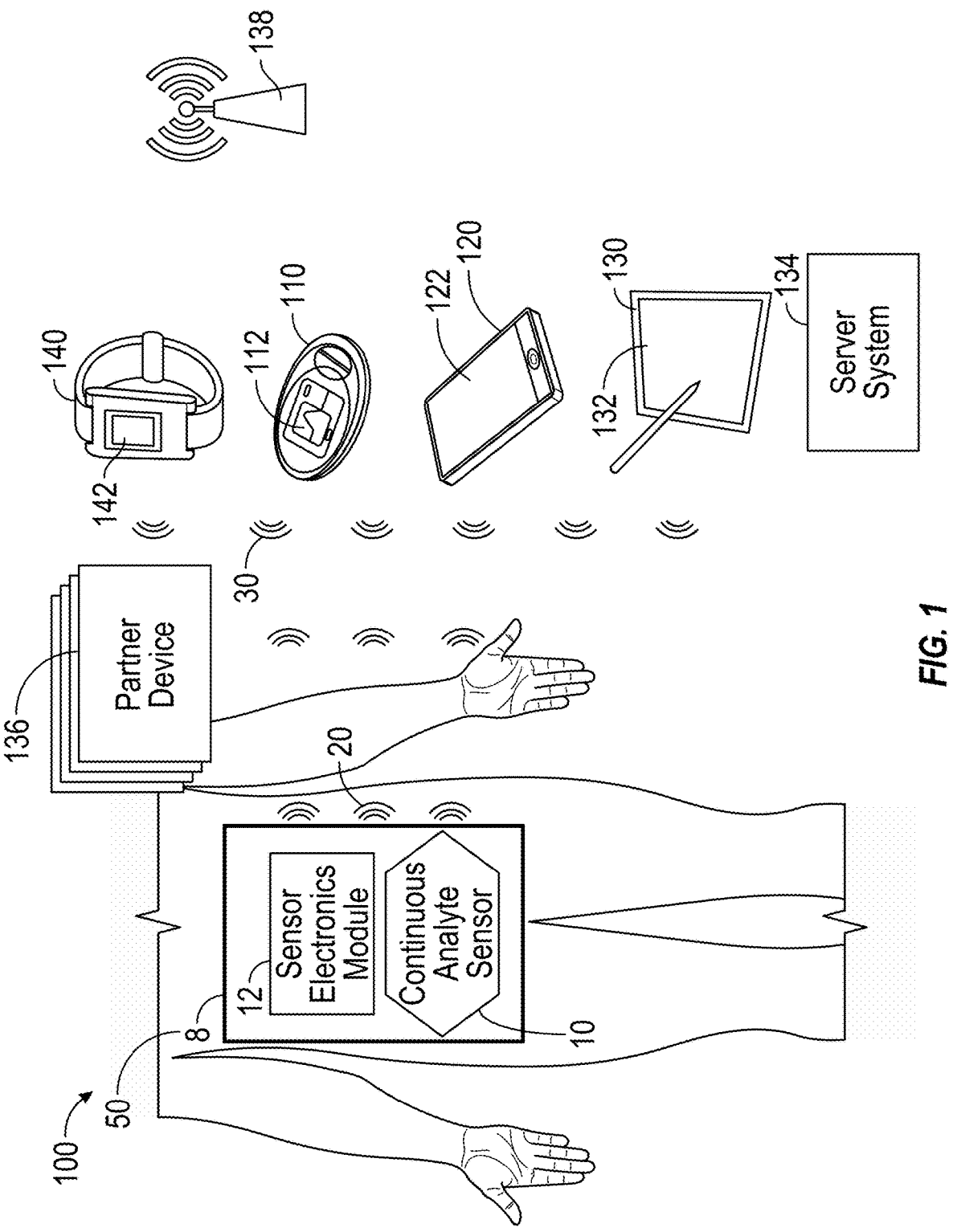
FIG. 1 illustrates aspects of an example system that may be used in connection with some embodiments.

The figures are described in greater detail in the description and examples below, are provided for purposes of illustration only, and merely depict typical or example embodiments of the disclosure. The figures are not intended to be exhaustive or to limit the disclosure to the precise form disclosed. It should also be understood that the disclosure may be practiced with modification or alteration, and that the disclosure may be limited only by the claims and the equivalents thereof.

DETAILED DESCRIPTION

Aspects of the present disclosure provide systems, methods, and devices for reducing power consumption or dissipation associated with an analyte sensor system. For example, in some cases, to help conserve battery power of an analyte sensor system, the analyte sensor system may be equipped with a power activation device or module, which may be a circuit, such as including one or more integrated chips (ICs). The power activation module may be configured to maintain the analyte sensor system in an OFF state in the absence of a trigger event and to transition the analyte sensor system into an ON state at an occurrence of the trigger event. One such power activation module includes a tunnel magnetoresistance (TMR) sensor. The TMR sensor may be configured to output a discrete signal in the presence of an applied magnetic field. This discrete signal may, in turn, be used to control the flow of current from a battery of the analyte sensor system and, consequently, whether the analyte sensor system is powered on or off.

While power consumption in the analyte sensor system is at its highest when the analyte sensor system is powered on, power may still be consumed or dissipated by the analyte sensor system when powered off. This power consumption/ dissipation while the analyte sensor system is powered off is due to certain electrical components within the analyte sensor system having to be continually powered to sense the output signal of the TMR sensor. Albeit comparatively low compared to when powered on, the power consumption experienced while the analyte sensor system is powered off can be problematic. For example, when the analyte sensor system is stored for substantial amounts of time, the power consumption that occurs while the analyte sensor system is powered off can reduce battery power to such a level that the analyte sensor system becomes unusable.

Accordingly, aspects of the present disclosure provide a power activation module for reducing power consumption or dissipation when an associated sensor system is powered off. Additionally, the power activation module may optionally include a single pole double-throw (SPDT) switch, allowing the power activation module to function as an ON/OFF/ RESET device so that electrical components within the analyte sensor system wake in a known state. Further, in some embodiments, the power activation module may also optionally include a LOCK input (e.g., pin) to disable a TMR sensor and avoid intermittent shutdown of the electrical components in the presence of an unexpected applied magnetic field. In some embodiments, the LOCK input may be bidirectional and provide status of the applied magnetic field from the TMR sensor and to prevent false wakeups during shipping of the sensor system, for example, when an applied magnetic field may vary. While certain embodiments are described as being with respect to an analyte sensor system as an example electronic device, it should be noted that the techniques herein may also apply to power activation of other suitable electronic devices (e.g., wearable devices).

The details of some example embodiments of the systems, methods, and devices of the present disclosure are set forth in this description and in some cases, in other portions of the disclosure. Other features, objects, and advantages of the disclosure will be apparent to one of skill in the art upon examination of the present disclosure, description, figures, examples, and claims. It is intended that all such additional systems, methods, devices, features, and advantages be included within this description (whether explicitly or by reference), be within the scope of the present disclosure, and be protected by one or more of the accompanying claims. System Overview and Example Configurations FIG. 1 depicts a system 100 that may be used in connection with embodiments of the present disclosure that involve gathering, monitoring, and/or providing information regarding analyte values present in a user's body, including for example the user's blood glucose values, other analytes, multiple multiplexed or simultaneous measured analytes, or the like. System 100 depicts aspects of analyte sensor system 8 that may be communicatively coupled to display devices 110, 120, 130, and 140, partner devices 136, and/or server system 134.

Analyte sensor system 8 in the illustrated embodiment includes analyte sensor electronics module 12 and analyte sensor 10 associated with analyte sensor electronics module 12. Analyte sensor electronics module 12 may be electrically and mechanically coupled to analyte sensor 10 before analyte sensor 10 is implanted in a user or host. Accordingly, analyte sensor 10 may not require a user to couple analyte sensor electronics module 12 to analyte sensor 10. For example, analyte sensor electronics module 12 may be physically/mechanically and electrically coupled to analyte sensor 10 during manufacturing, and this physical/mechanical and electrical connection may be maintained during shipping, storage, insertion, use, and removal of analyte sensor system 8. As such, the electro-mechanically connected components (e.g., analyte sensor 10 and analyte sensor electronics module 12) of analyte sensor system 8 may be referred to as a "pre-connected" system. Analyte sensor electronics module 12 may be in wireless communication (e.g., directly or indirectly) with one or more of display devices 110, 120, 130, and 140. In addition, or alternatively to display devices 110, 120, 130, and 140, analyte sensor electronics module 12 may be in wireless communication (e.g., directly or indirectly) with partner devices 136 and/or server system 134. Likewise, in some examples, display devices 110-140 may additionally or alternatively be in wireless communication (e.g., directly or indirectly) with partner devices 136 and/or server system 134. Various couplings shown in FIG. 1 can be facilitated with wireless access point (WAP) 138, as also mentioned below.

In certain embodiments, analyte sensor electronics module 12 includes electronic circuitry associated with measuring and processing analyte sensor data or information, including prospective algorithms associated with processing and/or calibration of the analyte sensor data/information. Analyte sensor electronics module 12 can be physically/ mechanically connected to analyte sensor 10 and can be integral with (non-releasably attached to) or releasably attachable to analyte sensor 10. Analyte sensor electronics module 12 may also be electrically coupled to analyte sensor 10, such that the components may be electromechanically coupled to one another. Analyte sensor electronics module 12 may include hardware, firmware, and/or software that enables measurement and/or estimation of levels of the analyte in a host/user via analyte sensor 10 (e.g., which may be/include a glucose sensor). For example, analyte sensor electronics module 12 can include one or more of a potentiostat, a power source for providing power to analyte sensor 10, other components useful for signal processing and data storage, and a telemetry module for transmitting data from the sensor electronics module to one or more display devices. Electronics can be affixed to a printed circuit board (PCB) within analyte sensor system 8, or platform or the like, and can take a variety of forms. For example, the electronics can take the form of an integrated circuit (IC), such as an Application-Specific Integrated Circuit (ASIC), a microcontroller, a processor, and/or a state machine.

Analyte sensor electronics module 12 may include sensor electronics that are configured to process sensor information, such as sensor data, and generate transformed sensor data and displayable sensor information. Examples of systems and methods for processing sensor analyte data are described in more detail herein and in U.S. Pat. Nos. 7,310,544 and 6,931,327 and U.S. Patent Publication Nos. 2005/0043598, 2007/0032706, 2007/0016381, 2008/0033254, 2005/0203360, 2005/0154271, 2005/0192557, 2006/0222566, 2007/0203966 and 2007/0208245, all of which are incorporated herein by reference in their entireties.

With further reference to FIG. 1, display devices 110, 120, 130, and/or 140 can be configured for displaying (and/or alarming) displayable sensor information that may be transmitted by analyte sensor electronics module 12 (e.g., in a customized data package that is transmitted to the display devices based on their respective preferences). Each of display devices 110, 120, 130, or 140 can (respectively) include a display such as touchscreen display 112, 122, 132, /or 142 for displaying sensor information and/or analyte data to a user and/or receiving inputs from the user. For example, a graphical user interface (GUI) may be presented to the user for such purposes. In embodiments, the display devices may include other types of user interfaces such as voice user interface instead of or in addition to a touchscreen display for communicating sensor information to the user of the display device and/or receiving user inputs. In embodiments, one, some, or all of display devices 110, 120, 130, 140 may be configured to display or otherwise communicate the sensor information as it is communicated from analyte sensor electronics module 12 (e.g., in a data package that is transmitted to respective display devices), without any additional prospective processing required for calibration and/or real-time display of the sensor data.

The plurality of display devices 110, 120, 130, 140 depicted in FIG. 1 may include a custom display device, for example, analyte display device 110, specially designed for displaying certain types of displayable sensor information associated with analyte data received from analyte sensor electronics module 12 (e.g., a numerical value and/or an arrow, in embodiments). In embodiments, one of the plurality of display devices 110, 120, 130, 140 includes a smartphone, such as a mobile phone, based on an Android, IOS, or other operating system, and configured to display a graphical representation of the continuous sensor data (e.g., including current and/or historic data).

As further illustrated in FIG. 1 and mentioned above, system 100 may also include WAP 138 that may be used to couple one or more of analyte sensor system 8, the plurality display devices 110, 120, 130, 140 etc., server system 134, and partner devices 136 to one another. For example, WAP 138 may provide WiFi and/or cellular or other wireless connectivity within system 100. Near Field Communication (NFC) may also be used among devices of system 100 for exchanging data, as well as for performing specialized functions, e.g., waking up or powering a device or causing the device (e.g., analyte sensor electronics module 12 and/or a transmitter) to exit a lower power mode or otherwise change states and/or enter an operational mode. Server system 134 may be used to collect analyte data from analyte sensor system 8 and/or the plurality of display devices, for example, to perform analytics thereon, generate universal or individualized models for glucose levels and profiles, provide services or feedback, including from individuals or systems remotely monitoring the analyte data, and so on. Partner device(s) 136, by way of overview and example, can usually communicate (e.g., wirelessly) with analyte sensor system 8, including for authentication of partner device(s) 136 and/or analyte sensor system 8, as well as for the exchange of analyte data, medicament data, other data, and/or control signaling or the like. Partner devices 136 may include a passive device in example embodiments of the disclosure. One example of partner device 136 may be an insulin pump for administering insulin to a user in response and/or according to an analyte level of the user as measured/approximated using analyte sensor system 8. For a variety of reasons, it may be desirable for such an insulin pump to receive and track glucose values transmitted from analyte sensor system 8 (with reference to FIG. 1 for example). One example reason for this is to provide the insulin pump a capability to suspend/activate/control insulin administration to the user based on the user's glucose value being below/above a threshold value.

Figure 2:
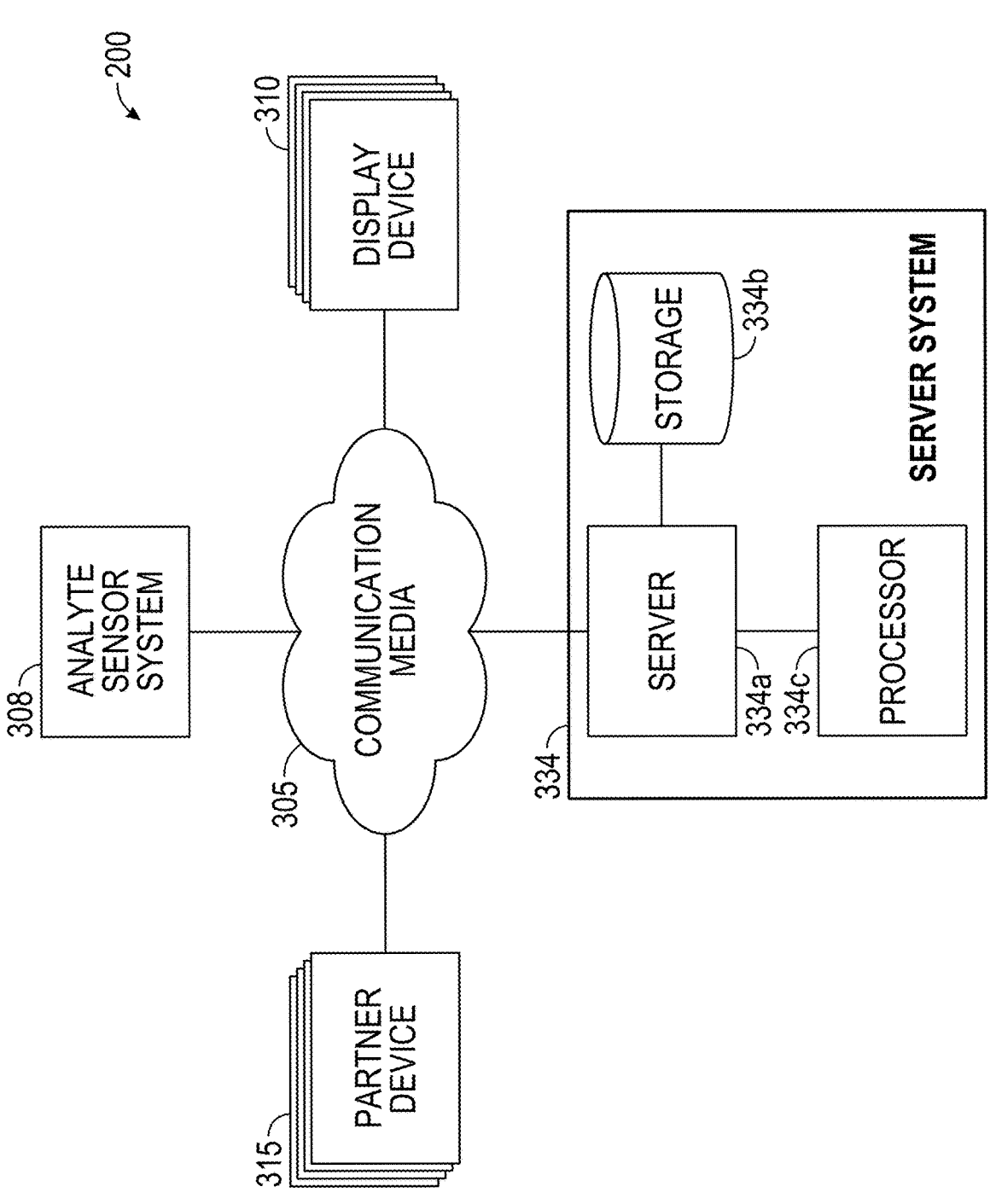
FIG. 2 illustrates aspects of an example system that may be used in connection with some embodiments.

Referring now to FIG. 2, system 200 is depicted. System 200 may be used in connection with implementing embodiments of the disclosed systems, methods, apparatuses, and/or devices, including, for example, aspects described above in connection with FIG. 1. By way of example, various below-described components of FIG. 2 may be used to provide wireless communication of analyte (e.g., glucose) data, for example among/between analyte sensor system 308, display devices 310, partner devices 315, and/or one or more server systems 334, and so on. In some cases, analyte sensor system 308 illustrated in FIG. 2 may be an example of the analyte sensor system 8 illustrated in FIG. 1. Additionally, in some cases, the display devices 310 illustrated in FIG. 2 may be examples of the display devices 110, 120, 130, and 140 illustrated in FIG. 1. Additionally, in some cases, partner devices 315 illustrated in FIG. 2 may be examples of the partner device 136 illustrated in FIG. 1.

As shown in FIG. 2, system 200 may include analyte sensor system 308, one or more display devices 310, and/or one or more partner devices 315. Additionally, in the illustrated embodiment, system 200 includes server system 334, which can in turn includes server 334a coupled to processor 334c and storage 334b. Analyte sensor system 308 may be coupled to display devices 310, partner devices 315, and/or server system 334 via communication media 305. Some details of the processing, gathering, and exchanging of data, and/or executing actions (e.g., providing medicaments or related instructions) by analyte sensor system 308, partner devices 315, and/or display device 310, etc., are provided below.

Analyte sensor system 308, display devices 310, and/or partner devices 315 may exchange messaging (e.g., control signaling) via communication media 305, and communication media 305 may also be used to deliver analyte data to display devices 310, partner devices 315, and/or server system 334. As alluded to above, display devices 310 may include a variety of electronic computing devices, such as, for example, a smartphone, tablet, laptop, wearable device, etc. Display devices 310 may also include analyte display device 110 that may be customized for the display and conveyance of analyte data and related notifications etc. Partner devices 315 may include medical devices, such as an insulin pump or pen, connectable devices, such as a smart fridge or mirror, key fob, and other devices.

In embodiments, communication media 305 may be based on one or more wireless communication protocols, such as for example Bluetooth, Bluetooth Low Energy (BLE), ZigBee, WiFi, IEEE 802.11 protocols, Infrared (IR), Radio Frequency (RF), 2G, 3G, 4G, 5G, etc., and/or wired protocols and media. It will also be appreciated upon studying the present disclosure that communication media can be implemented as one or more communication links, including in some cases, separate links, between the components of system 200, whether or not such links are explicitly shown in FIG. 2 or referred to in connection therewith. By way of illustration, analyte sensor system 308 may be coupled to display device 310 via a first link of communication media 305 using BLE, while display device 310 may be coupled to server system 334 by a second link of communication media 305 using a cellular communication protocol (e.g., 4G LTE/5G and the like). In embodiments, a BLE signal may be temporarily attenuated to minimize data interceptions. For example, attenuation of a BLE signal through hardware or firmware design may occur temporarily during moments of data exchange (e.g., pairing).

In embodiments, the elements of system 200 may be used to perform operations of various processes described herein and/or may be used to execute various operations and/or features described herein with regard to one or more disclosed systems and/or methods. Upon studying the present disclosure, one of skill in the art will appreciate that system 200 may include single or multiple analyte sensor systems 308, communication media 305, and/or server systems 334.

As mentioned, communication media 305 may be used to connect or communicatively couple analyte sensor system 308, display devices 310, partner devices 315, and/or server system 334 to one another or to a network. Communication media 305 may be implemented in a variety of forms. For example, communication media 305 may include one or more of an Internet connection, such as a local area network (LAN), a person area network (PAN), a wide area network (WAN), a fiber optic network, internet over power lines, a hard-wired connection (e.g., a bus), DSL, and the like, or any other kind of network connection or communicative coupling. Communication media 305 may be implemented using any combination of routers, cables, modems, switches, fiber optics, wires, radio (e.g., microwave/RF, AM, FM links etc.), and the like. Further, communication media 305 may be implemented using various wireless standards, such as Bluetooth®, BLE, Wi-Fi, IEEE 802.11, 3GPP standards (e.g., 2G GSM/GPRS/EDGE, 3G UMTS/CDMA2000, or 4G LTE/LTE-A/LTE-U, 5G, or subsequent generation), etc. Upon reading the present disclosure, one of skill in the art will recognize other ways to implement communication media 305 for communications purposes and will also recognize that communication media 305 may be used to implement features of the present disclosure using as of yet undeveloped communications protocols that may be deployed in the future.

Further referencing FIG. 2, server 334a may receive, collect, and/or monitor information, including analyte data, medicament data, and related information, from analyte sensor system 308, partner devices 315 and/or display devices 310, such as input responsive to the analyte data or medicament data, or input received in connection with an analyte monitoring application running on analyte sensor system 308 or display device 310, or a medicament delivery application running on display device 310 or partner device 315. As such, server 334a may receive, collect, and/or monitor information from partner devices 315, such as, for example, information related to the provision of medicaments to a user and/or information regarding the operation of one or more partner devices 315. Server 334a may also receive, collect, and/or monitor information regarding a user of analyte sensor system 308, display devices 310, and/or partner devices 315.

In embodiments, server 334a may be adapted to receive such information via communication media 305. This information may be stored in storage 334b and may be processed by processor 334c. For example, processor 334c may include an analytics engine capable of performing analytics on information that server 334a has collected, received, etc.

via communication media 305. In embodiments, server 334a, storage 334b, and/or processor 334c may be implemented as a distributed computing network, such as a Hadoop® network, or as a relational database or the like. The aforementioned information may then be processed at server 334a such that services may be provided to analyte sensor system 308, display devices 310, partner devices 315, and/or a user(s) thereof. For example, such services may include diabetes management feedback for the user.

In embodiments, a database may be implemented in server system 334 that may pair user accounts to one or more analyte sensor systems 308 using communication media 305. Based on, for example, an expected lifetime of individual components or one or more groups of components of analyte sensor system 308, or analyte sensor system 308 as a whole, and/or based on diagnostic feedback received by analyte sensor system 308, server system 334 may be able to determine if a given analyte sensor system 308 or component or group(s) of components thereof is expired or passed its useful life. A user may receive an indication, notification, alert, or warning, for example, on display device 310 and/or through analyte sensor system 308, from server system 334, that analyte sensor system 308 or a component or group(s) of components thereof has expired or passed its useful life or will do so soon or within a given amount of time. In embodiments, a user may receive an indication, notification, alert, or warning on display device 310 from server system 334 about the expected lifetime of analyte sensor system 308 or a component or group(s) of components thereof.

Server 334a may include, for example, an Internet server, a router, a desktop or laptop computer, a smartphone, a tablet, a processor, a module, or the like, and may be implemented in various forms, including, for example, an integrated circuit or collection thereof, a printed circuit board or collection thereof, or in a discrete housing/package/ rack or multiple of the same. In embodiments, server 334a at least partially directs communications made over communication media 305. Such communications may include the delivery of analyte data, medicament data, and/or messaging related thereto (e.g., advertisement, authentication, command, or other messaging). For example, server 334a may process and exchange messages between and/or among analyte sensor system 308, display devices 310, and/or partner devices 315 related to frequency bands, timing of transmissions, security/encryption, alarms, alerts, notifications, and so on. Server 334a may update information stored on analyte sensor system 308, partner devices 315, and/or display devices 310, for example, by delivering applications thereto or updating the same, and/or by reconfiguring system parameters or other settings of analyte sensor system 308, partner devices 315, and/or display devices 310. Server 334a may send/receive information to/from analyte sensor system 308, partner devices 315, and/or display devices 310 in real time, periodically, sporadically, or on an event-drive basis. Further, server 334a may implement cloud computing capabilities for analyte sensor system 308, partner devices 315, and/or display devices 310.

With the above description of aspects of the presently disclosed systems and methods for wireless communication of analyte data, examples of some specific features of the present disclosure will now be provided. It will be appreciated by one of skill in the art upon studying the present disclosure that these features may be implemented using aspects and/or combinations of aspects of the example configurations described above, whether or not explicit reference is made to the same.

Analyte Data

Referring back to FIG. 1, as mentioned above, in embodiments, analyte sensor system 8 is provided for measurement of an analyte in a host or user. By way of an overview and an example, analyte sensor system 8 may be implemented as an encapsulated microcontroller that makes sensor measurements, generates analyte data (e.g., by calculating values for continuous glucose monitoring data), and engages in wireless communications (e.g., via Bluetooth and/or other wireless protocols) to send such data to remote devices (e.g., display devices 110, 120, 130, 140, partner devices 136, and/or server system 134).

Analyte sensor system 8 may include: analyte sensor 10 configured to measure a concentration or level of the analyte in the host, and analyte sensor electronics module 12 that is typically physically connected to analyte sensor 10 before analyte sensor 10 is implanted in a user. In some cases, the analyte sensor 10 may be a multi-analyte sensor capable for measuring multiple different types of analytes, such as glucose, lactate, potassium, and the like. In embodiments, analyte sensor electronics module 12 includes electronics configured to process a data stream associated with an analyte concentration measured by analyte sensor 10, in order to generate sensor information that includes raw sensor data, transformed sensor data, and/or any other sensor data, for example. Analyte sensor electronics module 12 may further be configured to generate analyte sensor information that is customized for respective display devices 110, 120, 130, 140, partner devices 136, and/or server system 134. Analyte sensor electronics module 12 may further be configured such that different devices may receive different sensor information and may further be configured to wirelessly transmit sensor information to such display devices 110, 120, 130, 140, partner devices 136, and/or server system 134.

The term "analyte" as used herein is a broad term and is to be given its ordinary and customary meaning to a person of ordinary skill in the art (and is not to be limited to a special or customized meaning), and furthermore refers without limitation to a substance or chemical constituent in a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensor heads, devices, and methods is glucose. However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine;

dihydropteridine reductase; diptheria/tetanus antitoxin; erythrocyte arginase; erythrocyte protoporphyrin; esterase D; fatty acids/acylglycines; free-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; analyte-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani*, leptospira, measles/mumps/rubella, *Mycobacterium leprae, Mycoplasma pneumoniae*, Myoglobin, *Onchocerca volvulus*, parainfluenza virus, *Plasmodium falciparum*, poliovirus, *Pseudomonas aeruginosa*, respiratory syncytial virus, *Rickettsia* (scrub typhus), *Schistosoma mansoni, Toxoplasma gondii, Treponema pallidum, Trypanosoma cruzi/rangeli*, vesicular *stomatis* virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; elements; trace transferring; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids can also constitute analytes in certain embodiments. The analyte can be naturally present in the biological fluid, for example, a metabolic product, a hormone, an antigen, an antibody, and the like. Alternatively, the analyte can be introduced into the body, for example, a contrast agent for imaging, a radioisotope, a chemical agent, a fluorocarbon-based synthetic blood, or a drug or pharmaceutical composition, including but not limited to insulin; ethanol; *cannabis* (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-Dihydroxyphenylacetic acid (DOPAC), Homovanillic acid (HVA), 5-Hydroxytryptamine (5HT), and 5-Hydroxyindoleacetic acid (FHIAA).

Analyte Sensor System

As described to above with reference to FIG. 1, in some embodiments, analyte sensor 10 includes a continuous glucose sensor, for example, a subcutaneous, transdermal (e.g., transcutaneous), or intravascular device. In embodiments, such a sensor or device can continuously measure and analyze glucose measurements in the interstitial fluid, blood samples, etc., depending on whether the device is subcutaneous, transdermal, or intravascular. Analyte sensor 10 can use any method of analyte measurement, including for example glucose-measurement, including enzymatic, chemical, physical, electrochemical, spectrophotometric, polarimetric, calorimetric, iontophoretic, radiometric, immunochemical, and the like.

In embodiments where analyte sensor 10 is a glucose sensor, analyte sensor 10 can use any method, including invasive, minimally invasive, and non-invasive sensing techniques (e.g., fluorescence monitoring), or the like, to provide a data stream indicative of the concentration of glucose in a host. The data stream may be a raw data signal, which may be converted into a calibrated and/or filtered data stream that can be used to provide a useful value of glucose to a user, such as a patient or a caretaker (e.g., a parent, a relative, a guardian, a teacher, a doctor, a nurse, or any other individual that has an interest in the wellbeing of the host).

A glucose sensor can be any device capable of measuring the concentration of glucose. According to one example embodiment described below, an implantable glucose sensor may be used. However, it should be understood that the devices and methods described herein can be applied to any device capable of detecting a concentration of an analyte, glucose for example, and providing an output signal that represents the concentration of the analyte, again glucose for example (e.g., as a form of analyte data).

In embodiments, analyte sensor 10 is an implantable glucose sensor, such as described with reference to U.S. Pat. No. 6,001,067 and U.S. Patent Publication No. US-2005-0027463-A1. In embodiments, analyte sensor 10 is a transcutaneous glucose sensor, such as described with reference to U.S. Patent Publication No. US-2006-0020187-A1. In embodiments, analyte sensor 10 is configured to be implanted in a host vessel or extracorporeally, such as is described in U.S. Patent Publication No. US-2007-0027385-A1, co-pending U.S. Patent Publication No. US-2008-0119703-A1 filed Oct. 4, 2006, U.S. Patent Publication No. US-2008-0108942-A1 filed on Mar. 26, 2007, and U.S. Patent Application No. US-2007-0197890-A1 filed on Feb. 14, 2007. In embodiments, the continuous glucose sensor includes a transcutaneous sensor such as described in U.S. Pat. No. 6,565,509 to Say et al., for example. In embodiments, analyte sensor 10 is a continuous glucose sensor that includes a subcutaneous sensor such as described with reference to U.S. Pat. No. 6,579,690 to Bonnecaze et al. or U.S. Pat. No. 6,484,046 to Say et al., for example. In embodiments, the continuous glucose sensor includes a refillable subcutaneous sensor such as described with reference to U.S. Pat. No. 6,512,939 to Colvin et al., for example. The continuous glucose sensor may include an intravascular sensor such as described with reference to U.S. Pat. No. 6,477,395 to Schulman et al., for example. The continuous glucose sensor may include an intravascular sensor such as described with reference to U.S. Pat. No. 6,424,847 to Mastrototaro et al., for example.

Figure 3A:
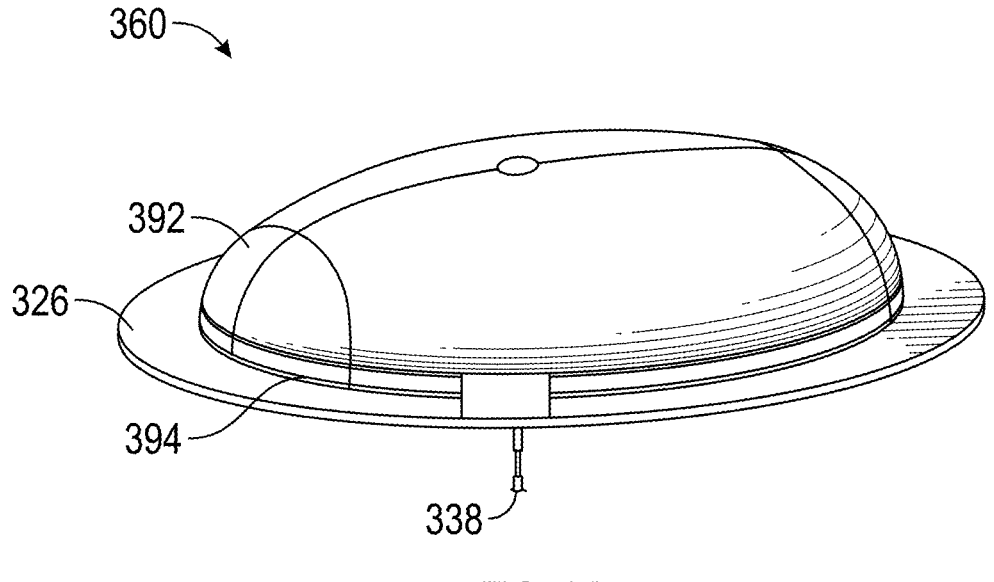
FIG. 3A is an example analyte sensor system, in accordance with some embodiments.

FIG. 3A illustrates a perspective view of an on-skin sensor assembly 360 that may be used in connection with an analyte sensor system 8, 308, in accordance with some embodiments. For example, on-skin sensor assembly 360 may include analyte sensor system 8, with reference by way of example to FIG. 1. On-skin sensor assembly 360 may include an outer housing with a first, top portion 392 and a second, bottom portion 394. In embodiments, the outer housing may include a clamshell design. On-skin sensor assembly 360 may include, for example, similar components as analyte sensor electronics module 12 described above in connection with FIG. 1, for example, a potentiostat, a power source for providing power to analyte sensor 10, signal processing components, data storage components, and a communication module (e.g., a telemetry module) for one-way or two-way data communication, a printed circuit board (PCB), an integrated circuit (IC), an Application-Specific Integrated Circuit (ASIC), a microcontroller, and/or a processor.

As shown in FIG. 3A, the outer housing may feature a generally oblong shape. The outer housing may further include aperture 396 disposed substantially through a center portion of outer housing and adapted for sensor 338 and needle insertion through a bottom of on-skin sensor assembly 360. In embodiments, aperture 396 may be a channel or elongated slot. On-skin sensor assembly 360 may further include an adhesive patch 326 configured to secure on-skin sensor assembly 360 to skin of the host. In embodiments, adhesive patch 326 may include an adhesive suitable for skin adhesion, for example a pressure sensitive adhesive (e.g., acrylic, rubber-based, or other suitable type) bonded to a carrier substrate (e.g., spun lace polyester, polyurethane film, or other suitable type) for skin attachment, though any suitable type of adhesive is also contemplated. As shown, adhesive patch 326 may feature an aperture 398 aligned with aperture 396 such that sensor 338 may pass through a bottom of on-skin sensor assembly 360 and through adhesive patch 326.

Figure 3B:
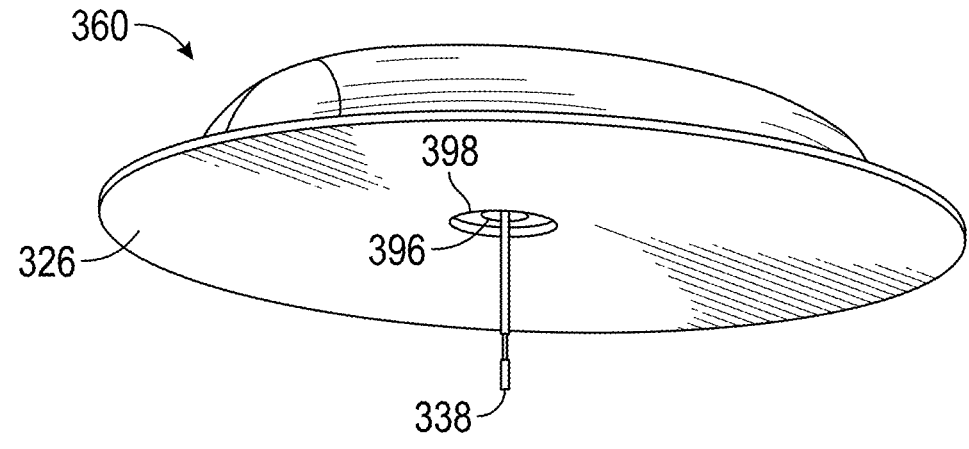
FIG. 3B is an example analyte sensor system, in accordance with some embodiments.

FIG. 3B illustrates a bottom perspective view of on-skin sensor assembly 360 of FIG. 3A. FIG. 3B further illustrates aperture 396 disposed substantially in a center portion of a bottom of on-skin sensor assembly 360, and aperture 398, both adapted for sensor 338 and needle insertion.

Figure 4:
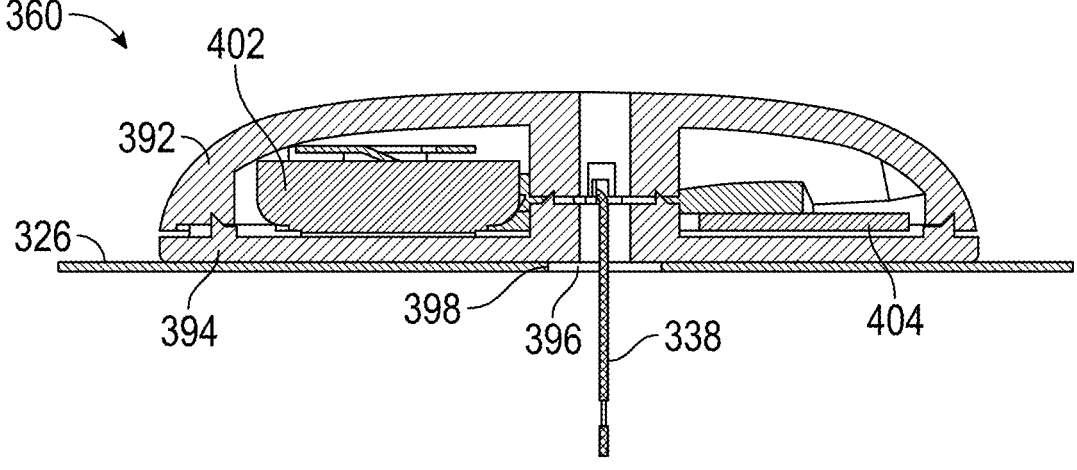
FIG. 4 illustrates aspects of an example analyte sensor system, in accordance with some embodiments.

FIG. 4 illustrates a cross-sectional view of on-skin sensor assembly 360 of FIGS. 3A and 3B. FIG. 4 illustrates first, top portion 392 and second, bottom portion 394 of the outer housing, adhesive patch 326, aperture 396 in the center portion of on-skin sensor assembly 360, aperture 398 in the center portion of adhesive patch 326, and sensor 338 passing through aperture 396. The electronics unit, previously described in connection with FIG. 3A, may further include circuit board 404 and battery 402 configured to provide power to at least circuit board 404.

Figure 5:
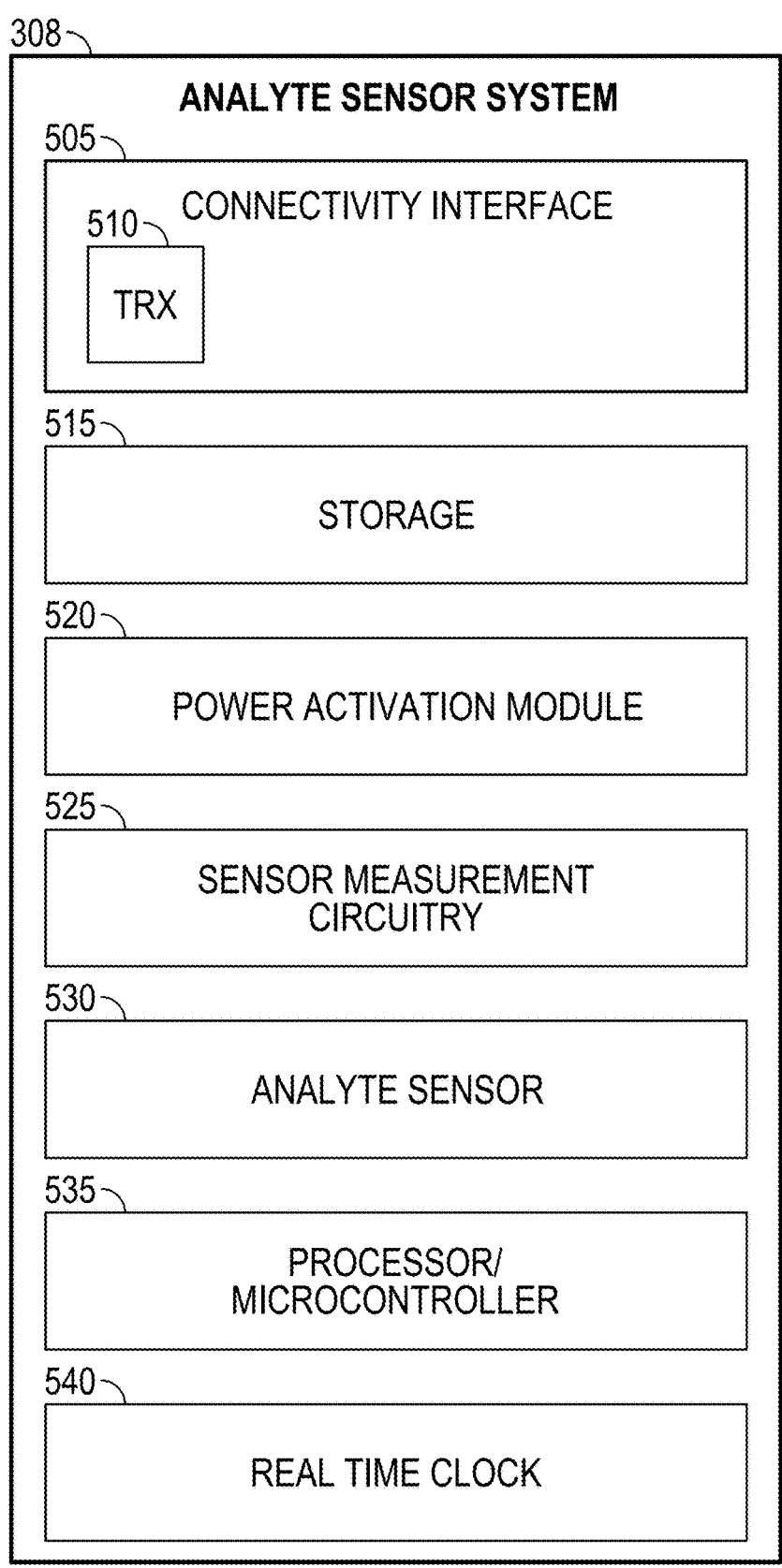
FIG. 5 illustrates aspects of an example analyte sensor system, in accordance with some embodiments.

Turning now to FIG. 5, a more detailed functional block diagram of analyte sensor system 308 (discussed above, for example, in connection with FIGS. 1 and 2) is provided. As noted above, the analyte sensor system 308 may be an example of the analyte sensor system 8 illustrated in FIG. 1. As shown in FIG. 5, analyte sensor system 308 may include analyte sensor 530 (e.g., which may be an example of the analyte sensor 10 illustrated in FIG. 1) coupled to analyte sensor measurement circuitry 525 for processing and managing sensor data. Sensor measurement circuitry 525 may be coupled to processor/microcontroller 535 (e.g., which may be part of analyte sensor electronics module 12 in FIG. 1). In some embodiments, processor/microcontroller 535 may perform part or all of the functions of sensor measurement circuitry 525 for obtaining and processing sensor measurement values from analyte sensor 530.

Processor/microcontroller 535 may be further coupled to a radio unit or transceiver 510 (e.g., which may be part of analyte sensor electronics module 12 in FIG. 1) for sending sensor and other data and receiving requests and commands and other signaling from an external device, such as display device 310 (referencing FIG. 2 by way of example). Display device 310 may be used to display or otherwise provide the sensor data (or analyte data) or data derived therefrom to a user, server system 334, and/or partner device 315. Partner device 315 may utilize sensor data or a derivative data derived therefrom in the administration of medicaments (e.g., insulin) and/or diabetes management guidance to the user. As used herein, the terms "radio unit" and "transceiver" may be used interchangeably and generally refer to a device that can wirelessly transmit and receive data. Analyte sensor system 308 may further include storage 515 (e.g., which may be part of analyte sensor electronics module 12 in FIG. 1) and real time clock (RTC) 540 (e.g., which may be part of analyte sensor electronics module 12 in FIG. 1), for storing and tracking sensor and other data.

As shown, analyte sensor system 308 may also include a power activation module 520. Power activation module 520 may use or include logic circuitry configured to perform functionalities as described herein with respect to detecting triggering events, such as the presence or absence of a magnetic field, and enabling activation of analyte sensor system 8, 308 based on the triggering events. Additional details regarding the power activation module 520 are discussed further herein.

Analyte sensor system 308, in example implementations, gathers analyte data using analyte sensor 530 and transmits the same or a derivative thereof to display device 310, partner device 315, and/or server system 334. Data points regarding analyte values may be gathered and transmitted over the life of analyte sensor 530. New measurements and/or related information may be transmitted often enough for a remote device/individual to adequately monitor analyte (e.g., glucose) levels.

It is to be appreciated that some details of the processing, gathering, and exchanging data by analyte sensor system 308, partner devices 315, and/or display device 310 etc. are provided elsewhere herein. It will be appreciated upon studying the present disclosure that analyte sensor system 308 may contain several like components that are described with respect to FIG. 1 or 2, at least for some embodiments herein. The details and uses of such like components may therefore be understood vis-a-vis analyte sensor system 308 even if not expressly described here with reference to FIG. 5.

Aspects Related to Power Activation for a Wearable Electronic Device

Patients with diabetes can benefit from real-time diabetes management guidance that is determined based on a physiological state of the patient. In certain cases, the physiological state of the patient is determined using diagnostics systems, such as an analyte sensor system (e.g., analyte sensor system 8 and/or analyte sensor system 308). In some embodiments, analyte sensor system 308 may be configured to measure glucose levels and inform a patient about the identification and/or prediction of adverse glycemic events, such as hyperglycemia and hypoglycemia. Additionally, the analyte sensor system 308 may be configured to help inform the type of guidance provided to the patient in response to these adverse glycemic events.

For example, the analyte sensor system 308 may be worn by a patient and configured to continuously measure the patient's glucose levels over time using a continuous analyte sensor, such as the analyte sensor 530. The measured glucose levels may then be processed by the analyte sensor system 308 (e.g., by the processor/microcontroller 535) to identify and/or predict adverse glycemic events, and/or to provide guidance to the patient for treatment and or actions to abate or prevent the occurrence of such adverse glycemic events. To perform and process these measurements, the analyte sensor system 308 may be equipped with a power source, such as a battery. When the analyte sensor system 308 is powered on, power from the battery may be consumed by different components of the analyte sensor system 308, such as one or more sensors (e.g., sensor measurement circuitry 525, analyte sensor 530, etc.), microprocessors (e.g., processor/microcontroller 535), transmitters (e.g., connectivity interface 505), and the like. Because the amount of power that may be stored within a battery is limited, power consumption in analyte sensor systems is a primary concern.

To help conserve battery power of a continuous glucose monitor, the analyte sensor system 308 may be equipped with a power activation module, such as the power activation module 520. The power activation module 520 may be designed to maintain the analyte sensor system 308 in an OFF state in the absence of a trigger event and to transition the analyte sensor system 308 into an ON state at an occurrence of the trigger event. In some embodiments, the power activation module 520 may include a tunnel magnetoresistance (TMR) sensor to maintain the analyte sensor system 308 in the OFF state in the absence of a trigger event. For example, the TMR sensor may be configured to output a discrete signal in the presence of an applied magnetic field. This discrete signal may, in turn, be used to control the flow of current from a battery of the analyte sensor system 308 and, consequently, whether the analyte sensor system 308 is powered on or off.

Figure 6:
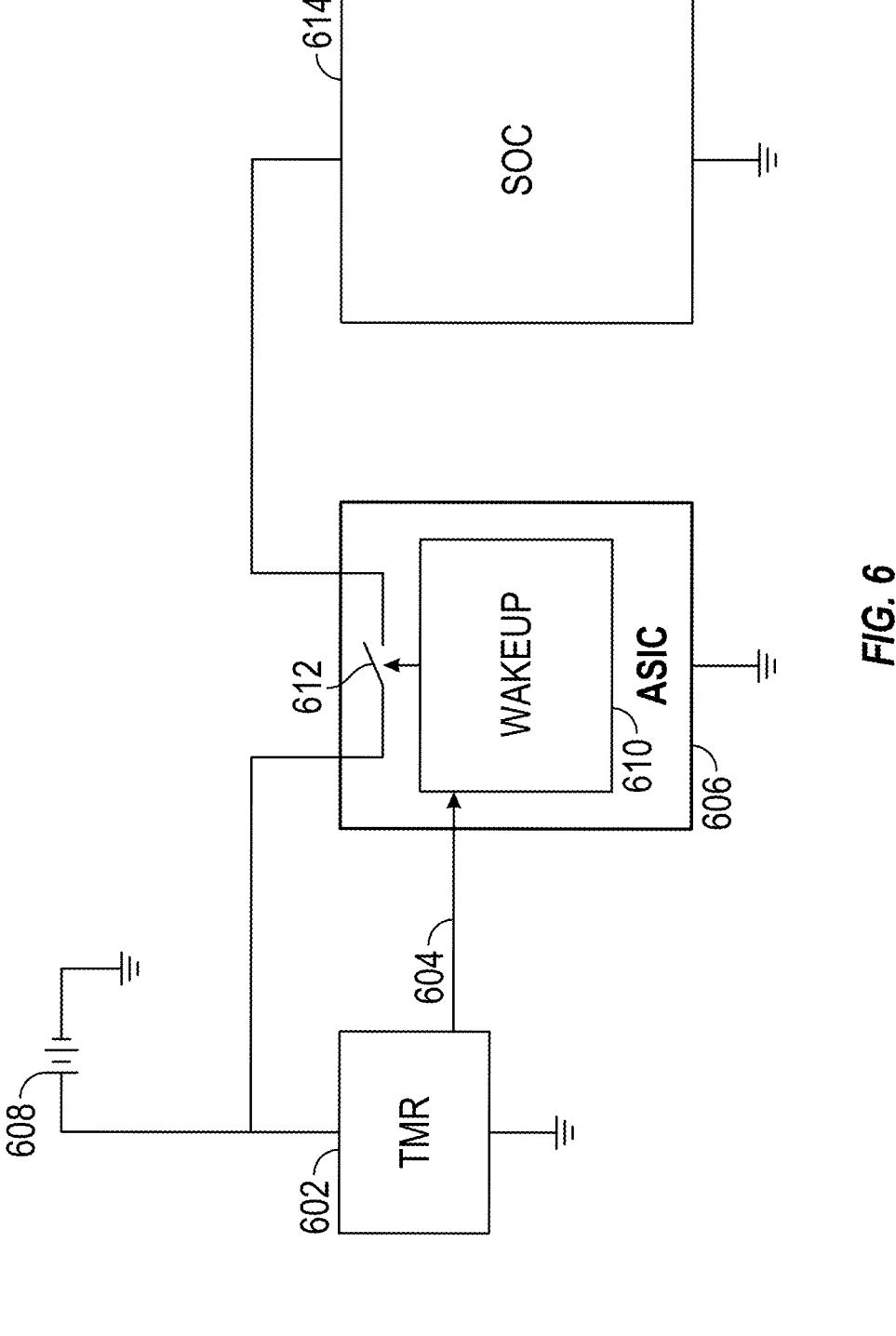
FIG. 6 illustrates an example power activation module incorporating a tunnel magnetoresistance sensor.

FIG. 6 illustrates an example power activation module 600 incorporating a TMR sensor 602. In some embodiments, the power activation module 600 may be an example of, or incorporated in, the power activation module 520 illustrated in FIG. 5. When a magnetic field is applied to or is near the TMR sensor 602, an output signal of the TMR sensor 602 may be configured to be low or zero. In some embodiments, the applied magnetic field may be provided by a magnet that is included within an applicator or packaging of the analyte sensor system 308. For example, in some cases, when the analyte sensor system 308 is located within the applicator or packaging, the magnet included within the applicator or packaging may apply a magnetic field to the TMR sensor 602, causing the output signal of the TMR sensor 602 to be low. Conversely, when the analyte sensor system 308 is removed from the packaging and/or applicator, the magnetic field from the included magnet is removed from the TMR sensor 602 and, as a result, the output signal from the TMR sensor 602 may be driven high.

The output signal of the TMR sensor 602, as shown at 604, may be fed into an application-specific integrated circuit (ASIC) 606 that is continually powered by battery 608 and configured to sense the output of the TMR sensor 602. Accordingly, when the output signal of the TMR sensor 602 is low, a wake-up component 610 within the ASIC 606 is configured to maintain a switch 612 in the ASIC in an open position to prevent current flow from the battery 608 to one or more electrical components (e.g., sensor measurement circuitry 525, analyte sensor 530, processor/microcontroller 535, connectivity interface 505, etc.) within a system on chip (SoC) 614 of the analyte sensor system 308, maintaining the analyte sensor system 308 in the OFF state.

In some embodiments, when a magnetic field is not applied to or is far from the TMR sensor 602, such as when the analyte sensor system 308 is removed from the packaging and/or applicator, the output signal of the TMR sensor 602 may be configured to be high (e.g., a logical one). Accordingly, when the magnetic field is removed from the TMR sensor 602, the wake-up component 610 of the ASIC 606 senses the output signal 604 from the TMR sensor 602 and, thereafter, closes the switch 612, allowing for current to flow from the battery 608 to the one or more electrical components of the SoC 614, thereby allowing the analyte sensor system 308 to transition to the ON state. In some examples, the power activation module 600 may utilize a near field communication (NFC)-based wake up system in lieu of a TMR sensor 602. In some cases, the NFC-based wakeup system may utilize a loop antenna or coil to sense magnetic induction which may, in turn, provide a signal to the switch 612 to turn on. In such examples, a display device may provide a radio frequency (RF) trigger signal to the loop antenna when brought in close proximity to the analyte sensor system 308.

For purposes of conserving battery power of the battery 608, it is desirable to maintain the analyte sensor system 308 in the OFF state when not being used or worn by a patient, such as when the analyte sensor system 308 is still in its packaging and being stored or shipped. Thereafter, the analyte sensor system 308 may be transitioned into the ON state when removed from the packaging and actively being used or worn by the patent. In some embodiments, to achieve the transition from the OFF state (e.g., while not being used or worn) to the ON state (e.g., while being used or worn), a magnet may be included within the packaging or housing of the continuous glucose monitor. While the continuous glucose monitor resides in its packaging or housing, the magnet applies a magnetic field to the TMR sensor 602 included within the power activation module 600, maintaining the analyte sensor system 308 in the OFF state to conserve battery power. When the analyte sensor system 308 is removed from its packaging or housing, the magnetic field may no longer be applied to the TMR sensor 602, allowing the current from the battery 608 to flow and forcing the analyte sensor system 308 into the ON state.

While power consumption in analyte sensor system 308 is at its highest when the analyte sensor system 308 is powered on (e.g., in the ON state), power may still be consumed or dissipated by the analyte sensor system 308 when in the OFF state. This power consumption/dissipation while the analyte sensor system 308 is in the OFF state may be the result of the wake-up component 610 in the ASIC 606 having to be continually powered in order to sense whether the output signal of the TMR sensor 602 is high or low. Albeit comparatively low to the ON state, the power consumption in the OFF state can be problematic. For example, when the analyte sensor system 308 is stored for substantial amounts of time, this power consumption experienced in the OFF state can reduce battery power to such a level that the analyte sensor system 308 becomes unusable. As such, there is a need in the art for improved systems and methods for power management in wearable devices, such as the analyte sensor system 308, utilizing magnet-based power activation modules.

Accordingly, aspects of the present disclosure provide a power activation module for reducing power consumption or dissipation when an associated sensor system (e.g., analyte sensor system 308) is in an OFF state. Additionally, the power activation module includes a single pole double-throw (SPDT) switch, allowing the power activation module to function as an ON/OFF/RESET device so that transceivers (e.g., transceiver 510) within the sensor system wake in a known state. The power activation module also includes a LOCK input (e.g., pin) to disable a TMR sensor and avoid intermittent shutdown of transceivers in the analyte sensor system 308 in the presence of an unexpected applied magnetic field. Additionally, In some embodiments, the LOCK input may be bidirectional and provide status of the applied magnetic field from the TMR sensor and to prevent false wakeups during shipping of the sensor system, for example, when an applied magnetic field may vary.

Figure 7:
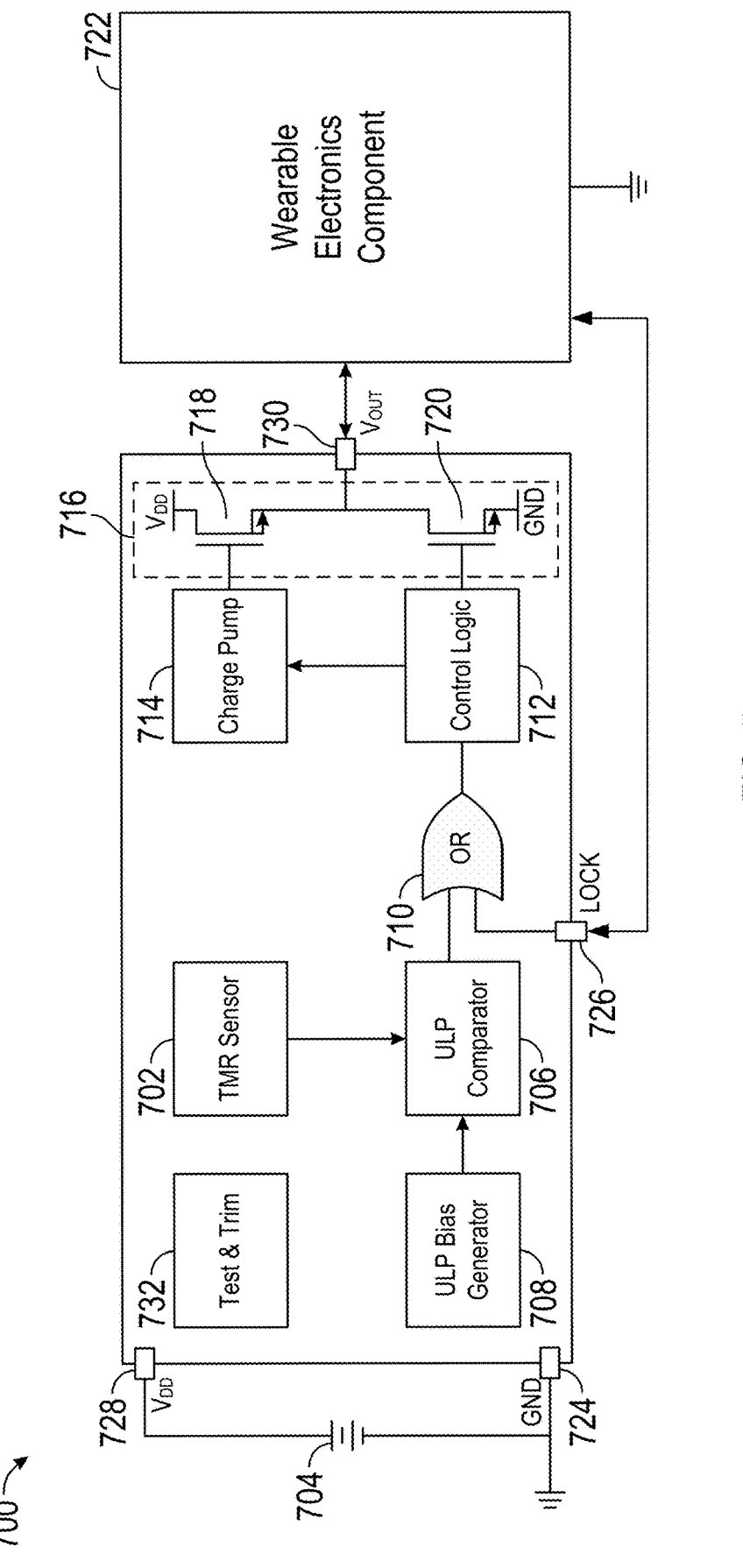
FIG. 7 illustrates an example circuit diagram of a power activation module.

FIG. 7 illustrates an example circuit diagram of a power activation module 700. The power activation module 700 may be part of a wearable electronics device, such as the power activation module 520 of the analyte sensor system 308, and may be used for powering a wearable electronics component 722 of the wearable electronics device. In some cases, the wearable electronics component 722 may include one or more electrical components of the analyte sensor system 308, such as sensor measurement circuitry 525, analyte sensor 530, processor/microcontroller 535, connectivity interface 505, etc.

As will be explained in greater detail below, the power activation module 700 includes a single pole double throw (SPDT) switch 716 configured to provide a path for current flow between a battery 704 associated with the power activation module 700, a wearable electronic component 722, and a ground terminal 724. Additionally, the SPDT switch 716 provides the wearable electronics device with ON/OFF/RESET functionality so that, when the wearable electronics device is powered on, a transceiver (e.g., transceiver 510) of the wearable electronics component 722 wakes up in a known state.

Additionally, the power activation module 700 includes a TMR sensor 702 configured to detect whether a magnetic field is applied to the TMR sensor 702. Based on the detection, the TMR sensor 702 is further configured to output a first digital output signal to operate the SPDT switch 716, controlling the current flow from the battery 704 to the wearable electronic component 722 of the wearable electronics device. In some cases, rather than employing the TMR sensor 702, the power activation module 700 may implement an NFC sensor that may be configured to detect whether a magnetic field is applied and, based on the detection, output a first digital output signal for controlling, at least in part, the SPDT switch 716 to control the current flow from the battery 704 to the wearable electronic component 722 of the wearable electronics device. In some cases, a different suitable sensor than an NFC sensor or TMR sensor may be used to detect whether an environmental condition (e.g., one or more types of signal such as a magnetic field/signal, temperature, etc.) is applied, and control the first digital output signal based on the detection.

Additionally, in certain aspects, the power activation module 700 optionally includes a lock pin 726 configured to receive a lock signal for power locking functionality, and optionally field monitoring functionality. The power locking functionality associated with the lock pin 726 prevents the wearable electronics component 722 of the wearable electronics device, such as a transceiver, from unintentionally powering off in the presence of a magnetic field. For example, in some cases, when the lock signal is received, the SPDT switch 716 is locked to allow current flow from the battery 704 to the wearable electronics component 722. Additionally, in certain embodiments, the field monitoring functionality associated with the lock pin provides the wearable electronics device with a capability of determining false wakeups.

As noted above, the power activation module 700 includes the TMR sensor 702. The TMR sensor 702 may be powered via an input pin 728 by a power supply, such as the battery 704. In certain aspects, the battery 704 provides an input voltage $V_{DD}$ ranging from about 1.1 Volts to 1.8 Volts. The voltage range of 1.1 Volts to 1.8 Volts is not intended to be limiting and other voltage ranges for $V_{DD}$ are possible. The TMR sensor 702 may be configured to detect whether a magnetic field is applied to the TMR sensor 702 and, based on the detection, output a first digital output signal. For example, in some embodiments, the TMR sensor 702 may be configured to output a low digital output signal (e.g., the first digital output signal comprises the low digital output signal) when a magnetic field applied to the TMR sensor 702 reaches an operate field threshold of the TMR sensor. Conversely, the TMR sensor 702 may be configured to output a high digital output signal (e.g., the first digital output signal comprises the high digital output signal) when the magnetic field is reduced to below a release field threshold of the TMR sensor 702. In other embodiments, the TMR sensor 702 may be configured to output a high digital output signal when the magnetic field is applied to the TMR sensor 702 and output a low digital output signal when the magnetic flied is not applied to the TMR sensor.

As shown, the power activation module 700 also includes a comparator, such as an ultra-low power (ULP) comparator 706, configured to receive the first digital output signal from the TMR sensor 702. The ULP comparator 706 may be further configured to compare a voltage of the first digital output signal of the TMR sensor 702 with a reference or bias voltage generated by, for example, a ULP bias generator 708 and output a second digital output signal based on whichever of the voltage of the first digital output signal or the reference voltage is larger. For example, when a voltage of a first digital output signal from the TMR sensor 702 is less than the reference voltage received from the ULP bias generator 708, the ULP comparator 706 is configured to output a low voltage (e.g., the second digital output signal comprises a low digital output signal). Conversely, when the voltage of the digital output signal from the TMR sensor 702 is greater than the reference voltage from the ULP bias generator 708, the ULP comparator 706 is configured to output a high voltage (e.g., the second digital output signal comprises a high digital output signal). Additionally, as shown, the power activation module 700 includes a test and trim component 732 configured to allow for the adjustment of the reference voltage generated by the ULP bias generator 708 as well as adjustment of a sensitivity of the TMR sensor 702 to an applied magnetic field.

In some embodiments, the second digital output signal from the ULP comparator 706 is then input into a first terminal of a logical OR gate 710. The logical OR gate 710 may be configured to output a third digital output signal based on the second digital output signal from the ULP comparator 706 and a lock signal received at a second terminal of the logical OR gate 710 via a lock pin of the power activation module 700.

When the voltage of the second digital output signal from the TMR sensor 702 is greater than the reference voltage from the ULP bias generator 708, the ULP comparator 706 outputs a high voltage to the first terminal of the logical OR gate 710. When either the voltage of the second digital output signal or a voltage of the lock signal is high, the logical OR gate 710 may be configured to output a high digital output signal (e.g., the third digital output signal comprises a high digital output signal). Thereafter, as shown, the third digital output signal may be input into a control logic component 712. When a voltage of the third digital output signal is high, this high voltage allows the control logic component 712 to transition to an ON state.

When in the ON state, the control logic component 712 is configured to output drive signals for controlling one or more transistors of the SPDT switch 716.

For example, in some embodiments, the control logic component 712 may output a first drive signal via a first output terminal to a charge pump component 714. In response to receiving the first drive signal from the control logic component 712, the charge pump component 714 may be configured to output a third drive signal via a second output terminal, applying a voltage higher than $V_{DD}$ to a gate terminal of a first transistor 718 of the SPDT switch 716, biasing the first transistor 718 ON. As shown, a drain terminal of the first transistor 718 is electrically coupled with the battery 704 and receives the input voltage $V_{DD}$ supplied by the battery 704. When the first transistor 718 is biased ON via the third drive signal from the charge pump component 714, current from the battery 704 is permitted to flow through the first transistor 718 (e.g., from the drain terminal of the first transistor 718 to a source terminal of the first transistor 718 electrically coupled with the wearable electronics component 722) and into the wearable electronics component 722 via an output pin 730, powering up the wearable electronics component 722. As shown, the voltage that is output from the first transistor 718 via the output pin 730 and supplied to the wearable electronics component 722 is known as $V_{out}$.

In some embodiments, when the voltage of the first digital output signal from the TMR sensor 702 is less than the reference voltage from the ULP bias generator 708, the ULP comparator 706 outputs a low voltage. Assuming a voltage of the lock signal of the lock pin 726 is also low, the low voltage associated with the first digital signal output of the TMR sensor 702, at least in part, maintains the control logic component 712 in the OFF state. When the control logic component 712 is in the OFF state, the control logic component 712 does not output the first drive signal to the charge pump component 714 (or outputs a low first drive signal), preventing the current flow from the battery 704 through the first transistor 718 and maintaining the wearable electronics component 722 in the OFF state.

For example, when a magnetic field is applied to the TMR sensor 702, the current from the battery 704 is prevented from flowing through the first transistor 718, which maintains the wearable electronics component 722 in the OFF state. However, when the magnetic field is removed from the TMR sensor 702, current from the battery 704 is permitted to flow through the first transistor 718, allowing the wearable electronics component 722 to transition to the ON state, as described above.

In some embodiments, after the one or more wearable electronic components are powered on, the wearable electronics component 722 may be configured to generate the lock signal and output the lock signal to the lock pin 726. For example, as shown, the lock signal may be input into the second terminal of the logical OR gate 710 disposed between the ULP comparator 706 and the control logic component 712. When applied (e.g., the lock signal is high), the lock signal locks the first transistor 718 to allow current flow from the battery 704 to the wearable electronics component 722. In other words, when the lock signal is applied by the wearable electronics component 722, the lock signal functionally removes the TMR sensor 702 from the power activation module 700 and forces the third digital output signal input into the control logic component 712 to be high regardless of whether a magnetic field is applied to the TMR sensor 702 or not. Accordingly, the lock signal functionality prevents the wearable electronics component 722 of the wearable electronics device, such as a transceiver (e.g., transceiver 510 of the analyte sensor system 308 in FIG. 5), from unintentionally powering off in the presence of a magnetic field.

Moreover, the lock signal may be used, in addition to field monitoring functionality of a microcontroller (e.g., processor/microcontroller 535) associated with the power activation module 700, to guard against false wakeups. For example, there may be instances in which the wearable electronics component 722 may be unintentionally woken up due to various environmental factors, such as vibration, loud noises, etc., In some cases, these environmental factors may be significant enough to cause fluctuations in the magnetic field sensed by the TMR sensor 702, causing the wearable electronics component 722 to be powered on. Unintentional or false wakeups of the wearable electronics component 722 may consume power from the battery 704 unnecessarily.

To help reduce power consumption associated with these false wakeups, upon waking up, a microcontroller of the wearable electronics component 722 (e.g., processor/microcontroller 535) may apply the lock signal, preventing the wearable electronics component 722 from being powered down. The microcontroller may then begin monitoring a magnetic field output signal from the TMR sensor 702 during a period of time. In some cases, due to the environmental factors, the magnetic field output signal from the TMR sensor 702 may vary during the monitoring period. As such, the microcontroller may determine, in view of the varying magnetic field output signal from the TMR sensor 702, whether the wakeup of the wearable electronics component 722 was a true (e.g., intentional) or false (e.g., unintentional) wakeup. For example, in some embodiments, based on the monitoring, when the magnetic field output signal from the TMR sensor 702 is greater than a magnetic field threshold for a threshold amount of time (e.g., during a defined time period such as a number of minutes), the microcontroller may determine that the wearable electronics component 722 was falsely woken up despite the variation in the magnetic field output signal from the TMR sensor 702. In response, the microcontroller may output a power down signal and cause the wearable electronics component 722 to de-assert the lock signal, allowing the wearable electronics component 722 to power down. However, when the magnetic field output signal from the TMR sensor 702 is less than or equal to the magnetic field threshold for the threshold amount of time, the microcontroller may determine that the wearable electronics component 722 was intentionally woken up despite the variation in the magnetic field output signal from the TMR sensor 702. In such embodiments, the microcontroller may continue asserting the lock signal to keep the wearable electronics component 722 powered on.

As noted above, in some embodiments, the TMR sensor 702 may be configured to output a high digital output signal when a magnetic field is applied to the TMR sensor 702 and output a low digital output signal when the magnetic flied is not applied to the TMR sensor. As a result, the wearable electronics component 722 may be configured to be woken up when a magnetic field is applied to the TMR sensor 702. In such embodiments, to detect a false wake up based on the monitoring by the microcontroller, when the magnetic field output signal from the TMR sensor 702 is less than a magnetic field threshold for a threshold amount of time (e.g., during a defined time period such as a number of minutes), the microcontroller may determine that the wearable electronics component 722 was falsely woken up despite the variation in the magnetic field output signal from the TMR sensor 702. In response, the microcontroller may output a power down signal and cause the wearable electronics component to de-assert the lock signal, allowing the wearable electronics component to power down. However, when the magnetic field output signal from the TMR sensor 702 is greater than or equal to the magnetic field threshold for the threshold amount of time, the microcontroller may determine that the wearable electronics component 722 was intentionally woken up despite the variation in the magnetic field output signal from the TMR sensor 702. In such embodiments, the microcontroller may continue asserting the lock signal to keep the wearable electronics component 722 powered on.

Figure 8:
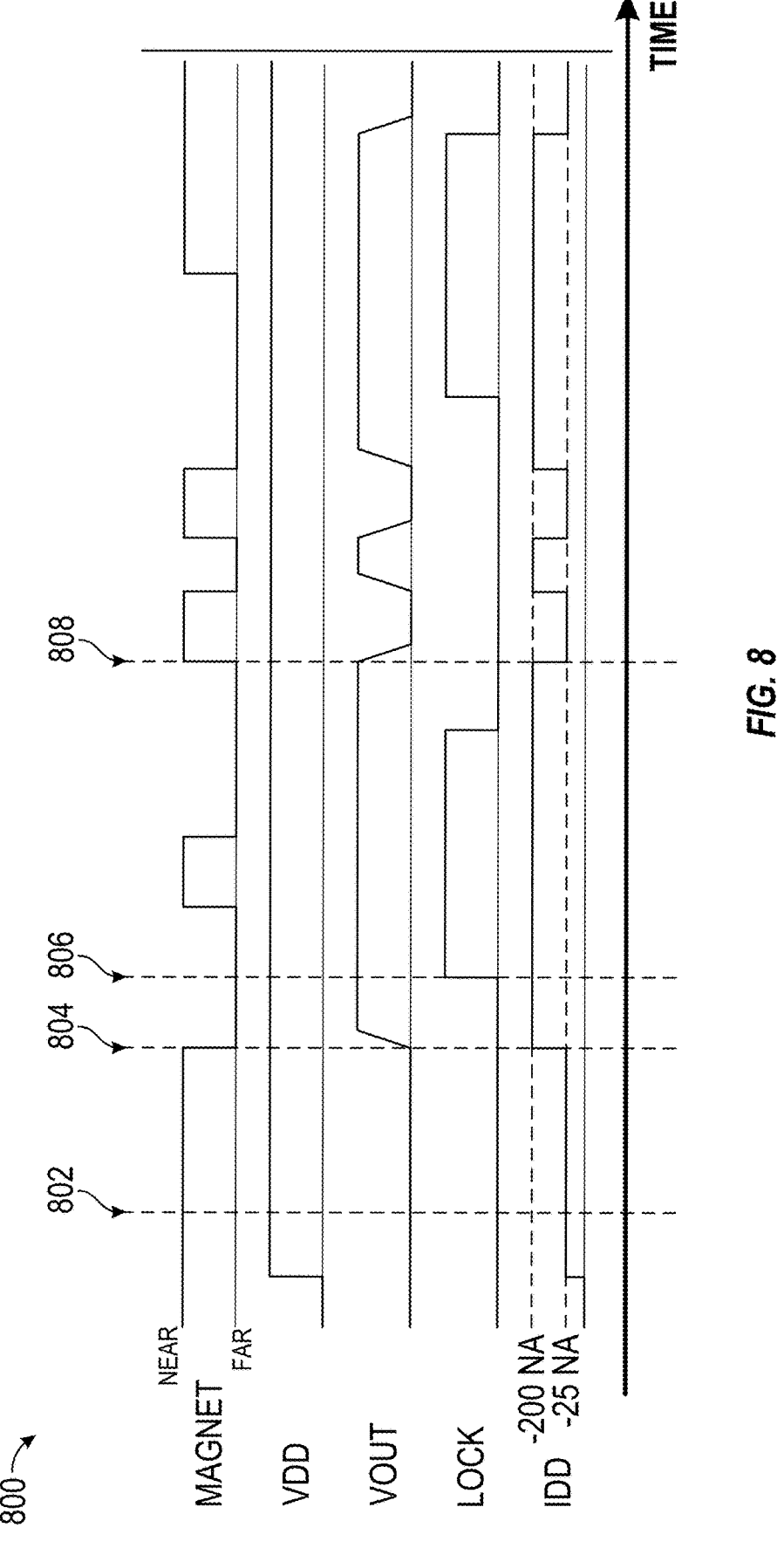
FIG. 8 illustrates an example signal timing diagram associated with the power activation module.

An example of the lock signal functionality is illustrated in FIG. 8. For example, FIG. 8 illustrates a signal timing diagram 800 associated with the power activation module 700 of FIG. 7. As shown at the beginning of the timing diagram at 802 in FIG. 8, when a magnet is near (and a magnetic field is applied to) the TMR sensor 702, the output voltage ($V_{out}$) applied to the output pin 730 (e.g., the voltage output from the power activation module 700 into the wearable electronics component 722) is low, maintaining the wearable electronics component 722 in the OFF state. At this point in time, when the wearable electronics component 722 is maintained in the OFF state, current (e.g., $I_{DD}$) from the battery 704 is prevented from flowing through the first transistor 718. However, as time progresses and the magnet is removed from the TMR sensor (and the magnetic field is no longer applied to the TMR sensor), as shown at 804, the power activation module 700 (e.g., via the control logic component 712 and charge pump component 714) biases the first transistor 718 on, allowing current (e.g., $I_{DD}$) from the battery 704 to flow into the wearable electronics component 722 and forcing the output voltage ($V_{out}$) applied to the output pin 730 high.

Thereafter, in some embodiments, the wearable electronics component 722 may output a high lock signal, as shown at 806. As can be seen, when the lock signal is high, the output voltage ($V_{out}$) of the power activation module remains high regardless of whether the magnet is close to or far from the TMR sensor 702, allowing the wearable electronics component 722 to remain in the ON state until the lock signal is removed and a magnetic field is applied to the TMR sensor 702 (e.g., a magnet is located near the TMR sensor 702). For example, in some embodiments, if it were necessary to put the wearable electronics device into storage, the wearable electronics component 722 may detect a power down signal (e.g., output by the microcontroller in the wearable electronics component 722). Thereafter, in response to the power down signal, the wearable electronics component 722 may prepare itself for power down and, after the wearable electronics component 722 is prepared for power down, the wearable electronics component 722 may de-assert the lock signal (e.g., output a low lock signal to the lock pin 726). Thereafter, a magnet can be subsequently applied and left applied to the TMR sensor 702, forcing the output voltage ($V_{out}$) and current ($I_{DD}$)) low and maintaining the wearable electronics component 722 in the OFF state, as shown at 808 in FIG. 8.

Returning to FIG. 7, as shown, the SPDT switch 716 of the power activation module 700 includes a second transistor 720. As shown, a gate terminal is coupled with, and driven by a second drive signal from, the control logic component 712. Additionally, as shown, a drain terminal of the second transistor device is electrically coupled with the source terminal of the first transistor and the one or more wearable electronic component, and a source terminal of the second transistor device is electrically coupled with the ground terminal.

According to aspects, the purpose of this second transistor 720 is to provide a conduction path to ground for the wearable electronics component 722 so that, when the wearable electronics component 722 is powered off, the wearable electronics component 722 will subsequently wake up in a known state. More specifically, for example, when devices are powered off but are not provided a conduction path to ground, electrical components included within these devices may not be able to fully discharge, retaining a particular amount of charge. This residual charge can result in electronics in the device to hang, causing a brownout in the device and the device to subsequently wake up in an unknown or undetermined state and possibly malfunction when subsequently powered on again.

Accordingly, to help avoid these issues, the power activation module 700 includes the second transistor 720 that may be driven by the control logic component 712 using a second drive signal, as noted above. By selectively driving the gate terminals of the first transistor 718 and second transistor 720, the control logic component 712 directs the current flow from the battery 704 along different conduction paths, as illustrated in FIG. 9, providing the wearable electronics device with true ON/OFF/RESET functionality.

Figure 9:
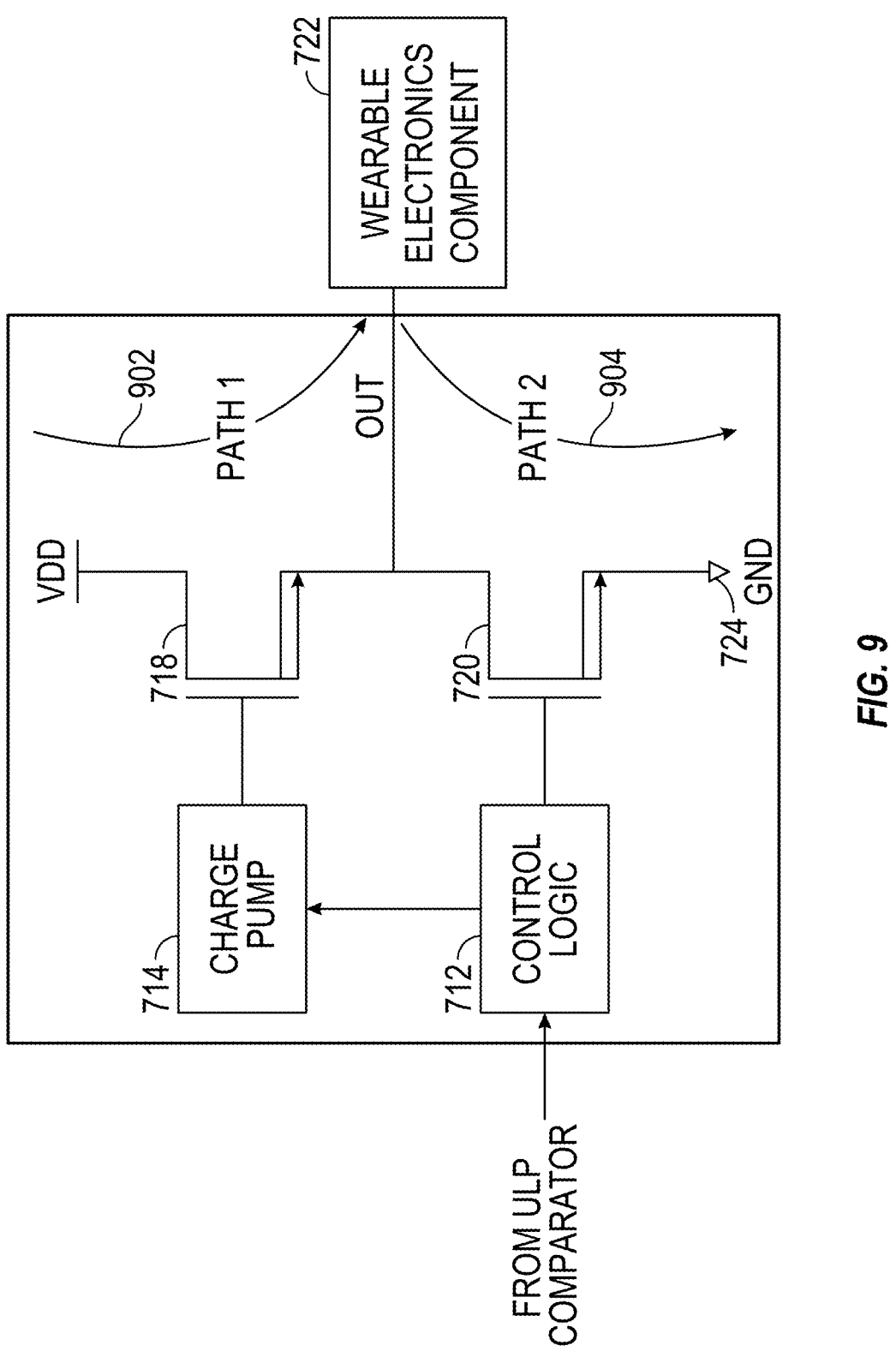
FIG. 9 illustrates different conduction paths associated with a single pole double throw (SPDT) switch.

For example, as illustrated in FIG. 9, when the wearable electronics component 722 is powered on, the second drive signal output via the first output terminal of the control logic component 712 and applied to the gate terminal of the second transistor 720 may be low such that the second transistor 720 is turned off and current from the battery 704 flows into the wearable electronics component 722 along conduction path 902. Thereafter, if the wearable electronics device is to be powered down, the wearable electronics component 722 may receive a power down signal, as described above, prepare itself for shutdown, and de-assert the lock signal from the lock pin 726.

Thereafter, the control logic component 712 may also receive a power down signal and, in response, control the first transistor 718 to stop the current flow from the battery 704 to the wearable electronics component 722. For example, in response to the power down signal, the control logic component 712 may be configured to output the first drive signal with a low voltage, forcing the charge pump component 714 to also output the third drive signal with a low voltage and, consequently, turning the first transistor 718 off and preventing the current flow from the battery 704 to the wearable electronics component 722 along conduction path 902. After the first transistor 718 has been turned off, the control logic component 712 may apply the second drive signal to the gate terminal of the second transistor 720 with a high voltage. The high voltage of the second drive signal applied to the gate terminal of the second transistor 720 permits current to flow from the wearable electronics component 722 to ground (e.g., via ground terminal 724) along conduction path 904, allowing electrical components of the wearable electronics component 722 to discharge and forcing the wearable electronics component 722 into a known state. A magnetic field may then be applied to the TMR sensor 702, allowing the wearable electronics device to transition to the OFF state. Thereafter, when the magnetic field is removed from the TMR sensor 702, the wearable electronics device may power up again in the known state.

As noted above, one goal of the power activation module 700 is to conserve battery power when the wearable electronics component 722 is in an OFF state (e.g., powered down). For example, in contrast to the power activation module 600 in FIG. 6 that requires the ASIC 606 to be continually powered in order to sense whether the output signal of the TMR sensor 602 is high or low (e.g., which consumes a significant amount of power), when the wearable electronics component 722 of the power activation module 700 is in the OFF state, the only components that continually need to be powered are the ULP comparator 706 and the control logic component 712, significantly reducing the amount of power consumed while the wearable electronics component 722 is in the OFF state. For example, while in the OFF state, the power activation module 600 may consume up to 1.2 microwatts while the power activation module 700 may only consume between 38 to 50 nanowatts.

While not specifically shown in FIG. 7, it should be understood that the individual components of the power activation module 700, such as the TMR sensor 702, the ULP comparator 706, the ULP bias generator 708, the control logic component 712, the charge pump component 714, the first transistor 718, and the second transistor 720, may each be, directly or indirectly, electrically coupled with the input pin 728 (e.g., supplying the voltage $V_{DD}$) as well as the ground terminal 724, forming an electrical circuit.

EXAMPLE CLAUSES

Implementation examples are described in the following numbered clauses:

Clause 1: A power activation module for powering one or more wearable electronic components, comprising: a switch configured to provide a path for current flow between a battery associated with the power activation module, the one or more wearable electronic components, and a ground terminal; a sensor configured to detect whether a signal is applied to the sensor and, based on the detection, output a first digital output signal for controlling, at least in part, the switch to control the current flow from the battery to the one or more wearable electronic components; and a lock pin configured to receive a lock signal, wherein when the lock signal is received, the switch is locked to allow current flow from the battery to the one or more wearable electronic components.

Clause 2: The power activation module of Clause 1, wherein the first digital output signal from the sensor comprises: a first low digital output signal when the sensor detects that the signal is applied to the sensor; and a first high digital output signal when the sensor detects that the signal is not applied to the sensor.

Clause 3: The power activation module of any one of Clauses 1-2, further comprising: a bias generator component configured to output a reference voltage; and a comparator component configured to: receive the first digital output signal from the sensor and the reference voltage from the bias generator component; compare a voltage of the first digital output signal with the reference voltage received from the bias generator component; and output a second digital output signal comprising: a second low digital output signal when, based on the comparison, the voltage of the first digital output signal is less than the reference voltage; and a second high digital output signal when, based on the comparison, the voltage of the first digital output signal is greater than the reference voltage.

Clause 4: The power activation module of Clause 3, further comprising: a control logic component configured to: receive an input signal, wherein the input signal is based on at least one of the second digital output signal from the comparator component or the lock signal from the lock pin; output a first drive signal via a first output terminal; and output a second drive signal; and a charge pump component configured to: receive the second drive signal from the control logic component; and output a third drive signal via a second output terminal.

Clause 5: The power activation module of Clause 4, wherein: the switch comprises a single pole double throw (SPDT) switch including, at least, a first transistor and a second transistor, the first transistor is configured to control the current flow from the battery to the one or more wearable electronic components, and the second transistor is configured to control the current flow from the one or more wearable electronic components to the ground terminal.

Clause 6: The power activation module of Clause 5, wherein: a gate terminal of the first transistor is coupled with the second output terminal of the charge pump component and configured to receive the third drive signal; a drain terminal of the first transistor is coupled with the battery; and a source terminal of the first transistor is coupled with the one or more wearable electronic components.

Clause 7: The power activation module of Clause 6, wherein: a gate terminal of the second transistor is coupled with the first output terminal of the control logic component; a drain terminal of the second transistor is coupled with the source terminal of the first transistor and the one or more wearable electronic components; and a source terminal of the second transistor is coupled with the ground terminal.

Clause 8: The power activation module of any one of Clauses 5-7, wherein, when the sensor detects that the signal is not applied to the sensor, the sensor is configured to control the SPDT switch to allow the current flow from the battery to the one or more wearable electronic components to power on the one or more wearable electronic components.

Clause 9: The power activation module of any one of Clauses 5-8, wherein the control logic component is further configured to: receive a power down signal; and in response to the power down signal: control the first transistor, via the second drive signal and the charge pump component, to stop the current flow from the battery to the one or more wearable electronic components; and control the second transistor, via the first drive signal, to permit the current flow from the one or more wearable electronic components to the ground terminal.

Clause 10: The power activation module of any one of Clauses 1-9, wherein the one or more wearable electronic components are configured to generate the lock signal and output the lock signal to the lock pin after the one or more wearable electronic components are powered on.

Clause 11: The power activation module of Clause 10, wherein the one or more wearable electronic components are further configured to: detect a power down signal, in response to the power down signal; prepare the one or more wearable electronic components for power down; and after the one or more wearable electronic components are prepared for power down, stop outputting the lock signal.

Clause 12: The power activation module of Clause 11, wherein: one or more wearable electronic components includes a microcontroller; the microcontroller is configured to monitor a magnetic field output signal from the sensor during a period of time; and when, during the period of time, the magnetic field output signal from the sensor is greater than a magnetic field threshold for a threshold amount of time, the microcontroller is configured to output the power down signal and cause one or more wearable electronic components to stop outputting the lock signal.

Clause 13: The power activation module of any one of Clauses 1-12, wherein: the sensor comprises one of a tunnel magnetoresistance (TMR) sensor or a near-field communication (NFC) sensor, and the signal comprises a magnetic field.

Clause 14: A method for operating a power activation module for powering one or more wearable electronic components, comprising: detecting, by a sensor of the power activation module, whether a signal is applied to the sensor; and outputting, from the sensor, a first digital output signal for controlling, at least in part, a switch to control current flow from a battery to the one or more wearable electronic components, wherein the switch is configured to provide a path for the current flow between the battery associated with the power activation module, the one or more wearable electronic components, and a ground terminal; and detecting whether a lock signal is received on a lock pin of the power activation module, wherein when the lock signal is received, the switch is locked to allow current flow from the battery to the one or more wearable electronic components.

Clause 15: The method of Clause 14, wherein the first digital output signal from the sensor comprises: a first low digital output signal when, based on the detecting, the signal is applied to the sensor; and a first high digital output signal when, based on the detecting, the signal is not applied to the sensor.

Clause 16: The method any one of Clauses 14-15, further comprising: outputting, from a bias generator component of the power activation module, a reference voltage; receiving, by a comparator component of the power activation module, the first digital output signal from the sensor and the reference voltage from the bias generator component; comparing, by the comparator component, a voltage of the first digital output signal with the reference voltage received from the bias generator component; and outputting, by the comparator component, a second digital output signal comprising: a second low digital output signal when, based on the comparison, the voltage of the first digital output signal is less than the reference voltage; and a second high digital output signal when, based on the comparison, the voltage of the first digital output signal is greater than the reference voltage.

Clause 17: The method of Clause 16, further comprising: receiving, by a control logic component of the power activation module, an input signal, wherein the input signal is based on at least one of the second digital output signal from the comparator component or the lock signal from the lock pin; outputting, by the control logic component, a first drive signal via a first output terminal; outputting, by the control logic component, a second drive signal; receiving, by a charge pump component of the power activation module, the second drive signal from the control logic component; and outputting, by a charge pump component, a third drive signal via a second output terminal.

Clause 18: The method of Clause 17, further comprising: controlling, by a first transistor of the switch, the current flow from the battery to the one or more wearable electronic components, wherein the switch comprises a single pole double throw (SPDT) switch including at least the first transistor and a second transistor; and controlling, by the second transistor, the current flow from the one or more wearable electronic components to the ground terminal.

Clause 19: The method of Clause 18, wherein: a gate terminal of the first transistor is coupled with the second output terminal of the charge pump component and configured to receive the third drive signal, a drain terminal of the first transistor is coupled with the battery, and a source terminal of the first transistor is coupled with the one or more wearable electronic components.

Clause 20: The method of Clause 19, wherein: a gate terminal of the second transistor is coupled with the first output terminal of the control logic component, a drain terminal of the second transistor is coupled with the source terminal of the first transistor and the one or more wearable electronic components, and a source terminal of the second transistor is coupled with the ground terminal.

Clause 21: The method of any one of Clauses 18-20, further comprising controlling the SPDT switch to allow the current flow from the battery to the one or more wearable electronic components to power on the one or more wearable electronic components when, based on the detecting, the signal is not applied to the sensor.

Clause 22: The method of any one of Clauses 18-21, further comprising: receiving, by the control logic component, a power down signal; and in response to the power down signal: controlling, by the control logic component, the first transistor, via the second drive signal and the charge pump component, to stop the current flow from the battery to the one or more wearable electronic components; and controlling, by the control logic component, the second transistor, via the first drive signal, to permit the current flow from the one or more wearable electronic components to the ground terminal.

Clause 23: The method of any one of Clauses 14-22, further comprising generating the lock signal and outputting the lock signal to the lock pin after the one or more wearable electronic components are powered on.

Clause 24: The method of Clause 23, further comprising detecting, by the wearable electronic components, a power down signal; preparing, by the wearable electronic components, the one or more wearable electronic components for power down in response to the power down signal; and stopping, by the wearable electronic components, outputting the lock signal after the one or more wearable electronic components are prepared for power down.

Clause 25: The method of Clause 24, further comprising: monitoring, by a microcontroller of the one or more wearable electronic components, a magnetic field output signal from the sensor during a period of time; and outputting, by the microcontroller, the power down signal and causing the one or more wearable electronic components to stop outputting the lock signal when, during the period of time, the magnetic field output signal from the sensor is greater than a magnetic field threshold for a threshold amount of time.

Clause 26: The method of any one of Clauses 14-25, wherein: the sensor comprises one of a tunnel magnetoresistance (TMR) sensor or a near-field communication (NFC) sensor, and the signal comprises a magnetic field.

ADDITIONAL CONSIDERATIONS

In this document, the terms "computer program medium" and "computer usable medium" and "computer readable medium", as well as variations thereof, are used to generally refer to transitory or non-transitory media such as, for example, main memory 1115, storage unit interface 1135, removable storage media 1125, and/or channel 1145. These and other various forms of computer program media or computer usable/readable media may be involved in carrying one or more sequences of one or more instructions to a processing device for execution. Such instructions embodied on the medium, may generally be referred to as "computer program code" or a "computer program product" or "instructions" (which may be grouped in the form of computer programs or other groupings). When executed, such instructions may enable the computing module 1100, circuitry related thereto, and/or a processor thereof or connected thereto to perform features or functions of the present disclosure as discussed herein (for example, in connection with methods described above and/or in the claims), including for example when the same is/are incorporated into a system, apparatus, device and/or the like.

Various embodiments have been described with reference to specific example features thereof. It will, however, be evident that various modifications and changes may be made thereto without departing from the broader spirit and scope of the various embodiments as set forth in the appended claims. The specification and figures are, accordingly, to be regarded in an illustrative rather than a restrictive sense. It will be appreciated that, for clarity purposes, the above description has described embodiments with reference to different functional units. However, it will be apparent that any suitable distribution of functionality between different functional units may be used without detracting from the invention. For example, functionality illustrated to be performed by separate computing devices may be performed by the same computing device. Likewise, functionality illustrated to be performed by a single computing device may be distributed amongst several computing devices. Hence, references to specific functional units are only to be seen as references to suitable means for providing the described functionality, rather than indicative of a strict logical or physical structure or organization.

Although described above in terms of various example embodiments and implementations, it should be understood that the various features, aspects and functionality described in one or more of the individual embodiments are not limited in their applicability to the particular embodiment with which they are described, but instead may be applied, alone or in various combinations, to one or more of the other embodiments of the present application, whether or not such embodiments are described and whether or not such features are presented as being a part of a described embodiment. Thus, the breadth and scope of the present application should not be limited by any of the above-described example embodiments.

Terms and phrases used in the present application, and variations thereof, unless otherwise expressly stated, should be construed as open ended as opposed to limiting. As examples of the foregoing: the term "including" should be read as meaning "including, without limitation" or the like; the term "example" is used to provide illustrative instances of the item in discussion, not an exhaustive or limiting list thereof; the terms "a" or "an" should be read as meaning "at least one," "one or more" or the like; the term "set" should be read to include one or more objects of the type included in the set; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Similarly, the plural may in some cases be recognized as applicable to the singular and vice versa. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic, circuitry, or other components, may be combined in a single package or separately maintained and may further be distributed in multiple groupings or packages or across multiple locations.

Additionally, the various embodiments set forth herein are described in terms of example block diagrams, flow charts, and other illustrations. As will become apparent to one of ordinary skill in the art after reading this document, the illustrated embodiments and their various alternatives may be implemented without confinement to the illustrated examples. For example, block diagrams and their accompanying description should not be construed as mandating a particular architecture or configuration. Moreover, the operations and sub-operations of various methods described herein are not necessarily limited to the order described or shown in the figures, and one of skill in the art will appreciate, upon studying the present disclosure, variations of the order of the operations described herein that are within the spirit and scope of the disclosure. It will be understood that each block of the flowchart illustrations, and combinations of blocks in the flowchart illustrations, can be implemented by execution of computer program instructions. These computer program instructions may be loaded onto a computer or other programmable data processing apparatus (such as a controller, microcontroller, microprocessor or the like) in a sensor electronics system to produce a machine, such that the instructions which execute on the computer or other programmable data processing apparatus create instructions for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks presented herein.

It should be appreciated that all methods and processes disclosed herein may be used in any glucose or other analyte monitoring system, continuous or intermittent. It should further be appreciated that the implementation and/or execution of all methods and processes may be performed by any suitable devices or systems, whether local or remote. Further, any combination of devices or systems may be used to implement the present methods and processes.

In addition, the operations and sub-operations of methods described herein may be carried out or implemented, in some cases, by one or more of the components, elements, devices, modules, circuitry, processors, etc. of systems, apparatuses, devices, environments, and/or computing modules described herein and referenced in various of figures of the present disclosure, as well as one or more sub-components, elements, devices, modules, processors, circuitry, and the like depicted therein and/or described with respect thereto. In such instances, the description of the methods or aspects thereof may refer to a corresponding component, element, etc., but regardless of whether an explicit reference is made, one of skill in the art will recognize upon studying the present disclosure when the corresponding component, element, etc. may be used. Further, it will be appreciated that such references do not necessarily limit the described methods to the particular component, element, etc. referred to. Thus, it will be appreciated by one of skill in the art that aspects and features described above in connection with (sub-) components, elements, devices, modules, and circuitry, etc., including variations thereof, may be applied to the various operations described in connection with methods described herein, and vice versa, without departing from the scope of the present disclosure.

What is claimed is:

1. A power activation module for powering one or more wearable electronic components, comprising:
   a switch configured to provide a power path for current flow between a battery associated with the power activation module, the one or more wearable electronic components, and a ground terminal; and
   a tunnel magnetoresistance (TMR) sensor powered by the battery and configured to detect whether a magnetic field is applied to the TMR sensor, the TMR sensor being further configured to output a first digital output signal in response to the presence or absence of the magnetic field, the first digital output signal being fed to downstream digital control logic for controlling, at least in part, the switch to control the current flow from the battery to the one or more wearable electronic components.

2. The power activation module of claim 1, wherein:
   the first digital output signal from the sensor comprises:
   a first low digital output signal when the sensor detects that the signal is applied to the sensor; and
   a first high digital output signal when the sensor detects that the signal is not applied to the sensor.

3. The power activation module of claim 1, further comprising:
   a bias generator component configured to output a reference voltage; and
   a comparator component configured to:
   receive the first digital output signal from the sensor and the reference voltage from the bias generator component;
   compare a voltage of the first digital output signal with the reference voltage received from the bias generator component; and
   output a second digital output signal comprising:
   a second low digital output signal when, based on the comparison, the voltage of the first digital output signal is less than the reference voltage; and
   a second high digital output signal when, based on the comparison, the voltage of the first digital output signal is greater than the reference voltage.

4. The power activation module of claim 3, further comprising:
   a control logic component configured to:
   receive an input signal, wherein the input signal is based on at least one of the second digital output signal from the comparator component or a lock signal from a lock pin of the power activation module;
   output a first drive signal via a first output terminal; and output a second drive signal; and a charge pump component configured to:

receive the second drive signal from the control logic component; and output a third drive signal via a second output terminal.

5. The power activation module of claim 4, wherein:

the switch comprises a single pole double throw (SPDT) switch including, at least, a first transistor and a second transistor;

the first transistor is configured to control the current flow from the battery to the one or more wearable electronic components; and the second transistor is configured to control the current flow from the one or more wearable electronic components to the ground terminal.

6. The power activation module of claim 5, wherein:

a gate terminal of the first transistor is coupled with the second output terminal of the charge pump component and configured to receive the third drive signal;

a drain terminal of the first transistor is coupled with the battery;

a source terminal of the first transistor is coupled with the one or more wearable electronic components;

a gate terminal of the second transistor is coupled with the first output terminal of the control logic component;

a drain terminal of the second transistor is coupled with the source terminal of the first transistor and the one or more wearable electronic components; and a source terminal of the second transistor is coupled with the ground terminal.

7. The power activation module of claim 5, wherein, when the sensor detects that the signal is not applied to the sensor, the sensor is configured to control the SPDT switch to allow the current flow from the battery to the one or more wearable electronic components to power on the one or more wearable electronic components.

8. The power activation module of claim 5, wherein the control logic component is further configured to:

receive a power down signal; and in response to the power down signal:

control the first transistor, via the second drive signal and the charge pump component, to stop the current flow from the battery to the one or more wearable electronic components; and control the second transistor, via the first drive signal, to permit the current flow from the one or more wearable electronic components to the ground terminal.

9. The power activation module of claim 1, wherein the one or more wearable electronic components are configured to generate a lock signal and output the lock signal to a lock pin of the power activation module after the one or more wearable electronic components are powered on.

10. The power activation module of claim 9, wherein the one or more wearable electronic components are further configured to:

detect a power down signal;

in response to the power down signal, prepare the one or more wearable electronic components for power down; and after the one or more wearable electronic components are prepared for power down, stop outputting the lock signal.

11. The power activation module of claim 10, wherein: one or more wearable electronic components includes a microcontroller;

the microcontroller is configured to monitor a magnetic field output signal from the sensor during a period of time; and when, during the period of time, the magnetic field output signal from the sensor is greater than a magnetic field threshold for a threshold amount of time, the microcontroller is configured to output the power down signal and cause one or more wearable electronic components to stop outputting the lock signal.

12. A method for operating a power activation module for powering one or more wearable electronic components, comprising:

detecting, by a tunnel magnetoresistance (TMR) sensor of the power activation module, whether a magnetic field is applied to the TMR sensor; and outputting, from the TMR sensor, a first digital output signal in response to the presence or absence of the magnetic field, the first digital output signal being fed to downstream digital control logic for controlling, at least in part, a switch to control current flow from a battery to the one or more wearable electronic components, wherein the switch is configured to provide a power path for the current flow between the battery associated with the power activation module, the one or more wearable electronic components, and a ground terminal.

13. The method of claim 12, wherein:

the first digital output signal from the sensor comprises:

a first low digital output signal when, based on the detecting, the signal is applied to the sensor; and a first high digital output signal when, based on the detecting, the signal is not applied to the sensor.

14. The method of claim 12, further comprising:

outputting, from a bias generator component of the power activation module, a reference voltage;

receiving, by a comparator component of the power activation module, the first digital output signal from the sensor and the reference voltage from the bias generator component;

comparing, by the comparator component, a voltage of the first digital output signal with the reference voltage received from the bias generator component;

outputting, by the comparator component, a second digital output signal comprising:

a second low digital output signal when, based on the comparison, the voltage of the first digital output signal is less than the reference voltage; and a second high digital output signal when, based on the comparison, the voltage of the first digital output signal is greater than the reference voltage.

15. The method of claim 14, further comprising:

receiving, by a control logic component of the power activation module, an input signal, wherein the input signal is based on at least one of the second digital output signal from the comparator component or a lock signal from a lock pin of the power activation module;

outputting, by the control logic component, a first drive signal via a first output terminal;

outputting, by the control logic component, a second drive signal;

receiving, by a charge pump component of the power activation module, the second drive signal from the control logic component; and outputting, by a charge pump component, a third drive signal via a second output terminal.

16. The method of claim 15, further comprising:

controlling, by a first transistor of the switch, the current flow from the battery to the one or more wearable electronic components, wherein the switch comprises a single pole double throw (SPDT) switch including at least the first transistor and a second transistor; and controlling, by the second transistor, the current flow from the one or more wearable electronic components to the ground terminal.

17. The method of claim 16, wherein:

a gate terminal of the first transistor is coupled with the second output terminal of the charge pump component and configured to receive the third drive signal;

a drain terminal of the first transistor is coupled with the battery;

a source terminal of the first transistor is coupled with the one or more wearable electronic components;

a gate terminal of the second transistor is coupled with the first output terminal of the control logic component;

a drain terminal of the second transistor is coupled with the source terminal of the first transistor and the one or more wearable electronic components; and a source terminal of the second transistor is coupled with the ground terminal.

18. The method of claim 16, further comprising controlling the SPDT switch to allow the current flow from the battery to the one or more wearable electronic components to power on the one or more wearable electronic components when, based on the detecting, the signal is not applied to the sensor.

19. The method of claim 16, further comprising:

receiving, by the control logic component, a power down signal; and in response to the power down signal:

controlling, by the control logic component, the first transistor, via the second drive signal and the charge pump component, to stop the current flow from the battery to the one or more wearable electronic components; and controlling, by the control logic component, the second transistor, via the first drive signal, to permit the current flow from the one or more wearable electronic components to the ground terminal.

20. The method of claim 12, further comprising:

generating a lock signal and outputting the lock signal to a lock pin of the power activation module after the one or more wearable electronic components are powered on;

monitoring, by a microcontroller of the one or more wearable electronic components, a magnetic field output signal from the sensor during a period of time;

outputting, by the microcontroller, a power down signal when, during the period of time, the magnetic field output signal from the sensor is greater than a magnetic field threshold for a threshold amount of time;

preparing, by the one or more wearable electronic components, the one or more wearable electronic components for power down in response to the power down signal; and stopping, by the wearable electronic components, outputting the lock signal after the one or more wearable electronic components are prepared for power down.

\*   \*   \*   \*   \*